United States Patent
Johnson et al.

(10) Patent No.: US 11,976,053 B2
(45) Date of Patent: May 7, 2024

(54) PROCESS OF PREPARING A PEPTIDE EPOXYKETONE IMMUNOPROTEASOME INHIBITOR, AND PRECURSORS THEREOF

(71) Applicant: KEZAR LIFE SCIENCES, South San Francisco, CA (US)

(72) Inventors: Henry Johnson, San Bruno, CA (US); Sean Dalziel, Burlingame, CA (US); Dustin McMinn, Pacifica, CA (US)

(73) Assignee: KEZAR LIFE SCIENCES, INC., South San Francisco, CA (US)

( * ) Notice: Subject to any disclaimer, the term of this patent is extended or adjusted under 35 U.S.C. 154(b) by 0 days.

(21) Appl. No.: 17/965,064

(22) Filed: Oct. 13, 2022

(65) Prior Publication Data

US 2023/0135100 A1 May 4, 2023

Related U.S. Application Data

(62) Division of application No. 17/015,450, filed on Sep. 9, 2020, now Pat. No. 11,498,907, which is a division of application No. 16/312,688, filed as application No. PCT/US2017/039975 on Jun. 29, 2017, now Pat. No. 10,781,192.

(60) Provisional application No. 62/356,178, filed on Jun. 29, 2016.

(51) Int. Cl.
| | |
|---|---|
| *C07D 295/13* | (2006.01) |
| *C07C 229/36* | (2006.01) |
| *C07D 295/15* | (2006.01) |
| *C07D 301/02* | (2006.01) |
| *C07D 303/12* | (2006.01) |
| *C07D 303/32* | (2006.01) |
| *C07D 303/46* | (2006.01) |

(52) U.S. Cl.
CPC .......... *C07D 295/13* (2013.01); *C07C 229/36* (2013.01); *C07D 295/15* (2013.01); *C07D 301/02* (2013.01); *C07D 303/12* (2013.01); *C07D 303/32* (2013.01); *C07D 303/46* (2013.01); *C07B 2200/13* (2013.01)

(58) Field of Classification Search
CPC .. C07D 295/13; C07D 295/15; C07D 303/12; C07C 229/36
See application file for complete search history.

(56) References Cited

U.S. PATENT DOCUMENTS

| | | |
|---|---|---|
| 4,522,811 A | 6/1985 | Eppstein et al. |
| 5,340,736 A | 8/1994 | Goldberg |
| 8,530,694 B2 | 9/2013 | Olhava et al. |
| 8,609,610 B2 | 12/2013 | Kisselev et al. |
| 8,609,654 B1 | 12/2013 | Shenk et al. |
| 8,697,646 B2 | 4/2014 | Phiasivongsa |
| 8,716,322 B2 | 5/2014 | Zhou et al. |
| 8,822,512 B2 | 9/2014 | Phiasivongsa et al. |
| 8,853,147 B2 | 10/2014 | Kirk et al. |
| 8,921,583 B2 | 12/2014 | Phiasivongsa et al. |
| 9,051,353 B2 | 6/2015 | Phiasivongsa et al. |
| 9,187,442 B2 | 11/2015 | Nishino et al. |
| 9,205,124 B2 | 12/2015 | Zhou et al. |
| 9,205,125 B2 | 12/2015 | Zhou et al. |
| 9,205,126 B2 | 12/2015 | Zhou et al. |
| 9,434,761 B2 | 9/2016 | McMinn et al. |
| 10,781,192 B2* | 9/2020 | Johnson ................ C07C 229/36 |
| 11,498,907 B2* | 11/2022 | Johnson ............... C07D 295/15 |
| 2009/0105156 A1 | 4/2009 | Phiasivongsa et al. |
| 2009/0203698 A1 | 8/2009 | Zhou et al. |
| 2011/0236428 A1 | 9/2011 | Kirk et al. |
| 2013/0150290 A1 | 6/2013 | Phiasivongsa et al. |
| 2014/0113855 A1 | 4/2014 | Jumaa et al. |
| 2014/0336106 A1 | 11/2014 | McMinn et al. |

FOREIGN PATENT DOCUMENTS

| | | |
|---|---|---|
| CN | 101525370 A | 9/2009 |
| CN | 104710507 A | 6/2015 |
| CN | 105143212 A | 12/2015 |
| EA | 018973 B1 | 12/2013 |
| EP | 1565193 A2 | 8/2005 |
| JP | 2016-515509 A | 5/2016 |

(Continued)

OTHER PUBLICATIONS

Bastin et al., Salt Selection and optimization procedures for pharmaceutical new chemical entities, Organic Process & Development, 4:427-35 (2000).

(Continued)

*Primary Examiner* — Deepak R Rao
(74) *Attorney, Agent, or Firm* — MARSHALL, GERSTEIN & BORUN LLP

(57) ABSTRACT

Disclosed herein are methods for preparing [(2S,3R)—N—[(2S)-3-(cyclopent-1-en-1-yl)-1-[(2R)-2-methyloxiran-2-yl]-1-oxopropan-2-yl]-3-hydroxy-3-(4-methoxyphenyl)-2-[(2S)-2-[2-(morpholin-4-yl)acetamido]propanamido] propanamide (compound "G"):

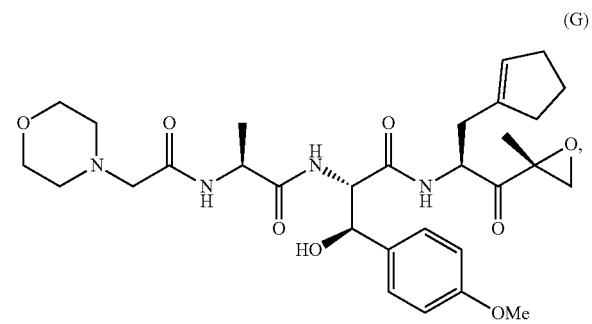

and precursors thereof.

20 Claims, 10 Drawing Sheets

(56) References Cited

FOREIGN PATENT DOCUMENTS

| WO | 98/10779 A1 | 3/1998 |
|---|---|---|
| WO | 2004/043374 A2 | 5/2004 |
| WO | 2012/151165 A1 | 11/2012 |
| WO | 2013/169897 A1 | 11/2013 |
| WO | 2014/056748 A1 | 4/2014 |
| WO | 2014/056954 A1 | 4/2014 |
| WO | 2014/152127 A1 | 9/2014 |
| WO | 2014/152134 A1 | 9/2014 |

OTHER PUBLICATIONS

Berge et al., Pharmaceutical salts, Journal of pharmaceutical sciences, American chemical society and American pharmaceutical association, 66(1):1-19 (1977).
Brittain, Developing an appropriate salt form for an active pharmaceutical ingredient : American pharmaceutical review—The review of American pharmaceutical business & technology, American pharmaceutical Review, 12(7):62-65 (2009).
Camille et al, Chapter 11 : Selected procedures for the preparation of pharmaceutically acceptable salts, Handbook or Pharmaceutical, 219-263 (2008).
Ciechanover et al., The Ubiquitin-Proteasome Proteolytic Pathway: Destruction for the Sake of Construction, Physiol Rev., 82:373-428, (2002).
Ciechanover, The ubiquitin-proteasome proteolytic pathway, Cell., 79:13-21 (1994).
Cohen, AIDS mood upbeat-for a change, Science, 267:959-960 (1995).
Collins, Endothelial nuclear factor-kappa B and the initiation of the atherosclerotic lesion, Lab. Invest., 68(5):499-508 (1993).
Dunetz et al., Large-Scale Applications of Amide Coupling Reagents for the Synthesis of Pharmaceuticals, Org. Process Res. Dev., 20:140-177 (2016).
Examiner initiated interview summary, U.S. Appl. No. 16/312,614, dated Dec. 11, 2019, 1 pages.
Flack et al., The use of X-ray crystallography to determine absolute configuration, Chirality, 20:681-690 (2008).
Garrett et al., Selective inhibitors of the osteoblast proteasome stimulate bone formation in vivo and in vitro, J clinical invest., 111:1771-1782 (2003).
Gonzalez et al., Proteasome function is required for encystation of entamoeba invadens, Arch med res 28 spec No. 139-140 (1997).
Han et al., Recent development of peptide coupling reagents in organic synthesis, Tetrahedron, 60:2447-2467 (2004).
Handbook for preparation of crystalline organic compounds—Principle and Knowhow, 57-79 (2008).
Hardy, The secret life of the hair follicle, Trends in genetics, 8:55-61 (1992).
Harris et al., Effects of transforming growth factor beta on bone nodule formation and expression of bone morphogenetic protein 2, osteocalcin, osteopontin, alkaline phosphatase, and type I collagen mRNA in long-term cultures of fetal rat calvarial osteoblasts, J. Bone Miner. Res., 9(6):855-863 (1994).
International Preliminary Report on Patentability for corresponding International Application No. PCT/US2017/039961, dated Jan. 10, 2019.
International Preliminary Report on Patentability for corresponding International Application No. PCT/US2017/039975, dated Jan. 10, 2019.
International Search Report and Written Opinion for corresponding International Application No. PCT/US2017/039961, dated Aug. 22, 2017.
International Search Report and Written Opinion for corresponding International Application No. PCT/US2017/039975, dated Oct. 23, 2017.
JP Office Action dated May 18, 2021 for JP Application No. 2018568267.
Kojima et al., Two-way cleavage of beta-amyloid protein precursor by multicatalytic proteinase, Fed. Eur. Biochem. Soc. 304:57-60 (1992).
Kumar et al., Effect of counterions on physicochemical properties of prazosin salts, AAPS pharmscitech 14(1):141-150 (2013).
Kumatori et al., Abnormally high expression of proteasomes in human leukemic cells, Proc. natl. acad. sci. USA 87:7071-7075 (1990).
Montalbetti et al., Amide bond formation and peptide coupling, Tetrahedron, 61:10827-10852 (2005).
Olovson et al., Oesophageal ulcerations and plasma levels of different alprenolol salts: Potential implications for the clinic, Acta pharmacol toxicol 58(1):55-60 (1986).
Palombella et al., The ubiquitin-proteasome pathway is required for processing the NF-kappa B1 precursor protein and the activation of NF-kappa B. Cell, 78(5): 773-85 (1994).
Paugam et al., Characterization and role of protozoan parasite proteasomes, Trends parasitol., 19:55-59 (2003).
Paulekuhn et al., Trends in active pharmaceutical ingredient salt selection based on analysis of the orange book database, J. Med. Chem., 50(26):6665-6672 (2007).
Pharmaceutical Salts, pp. 334-345, Retrieved from the Internet: URL:http://phoenix.tuwien.ac.at/pdf/pharmaceutical salts/Pharmaceutical_ salts.pdf (1958).
Qureshi et al., The proteasome as a lipopolysaccharide-binding protein in macrophages: Differential effects of proteasome inhibition on lipopolysaccharide-induced signaling events, J. immunology, 171:1515-1525 (2003).
Requirement for Restriction/Election received for U.S. Appl. No. 16/312,688, dated Sep. 18, 2019, 8 pages.
Requirement for Restriction/Election, U.S. Appl. No. 16/312,614, dated Dec. 11, 2019, 9 pages.
Saal et al., Pharmaceutical salts: A summary on doses of salt formers from the orange book, European journal of pharmaceutical sciences, 49(4):614-623, (2013).
Shimada et al., Proteasome inhibitors improve the function of mutant lysosomal Alpha-glucosidase in fibroblasts from Pompe disease patient carrying c.546G>T mutation, Biochem. biophys. res. commun., 415(2):274-8 (2011).
Simsek et al., Hepatitis B virus large and middle glycoproteins are degraded by a proteasome pathway in glucosidase-inhibited cells but not in cells with functional glucosidase enzyme, J. virol., 79(20):12914-12920 (2005).
Stahly, The importance of selection of salts, and screening of polymorphism of crystals in pharmaceuticals, Pharm., 66(6):435-439 (2006).
Szalay et al., Ongoing coxsackievirus myocarditis is associated with increased formation and activity of myocardial immunoproteaseomes, Am. J. Pathol., 168(5):1542-1552 (2006).
Thanos et al., NF-kappaB: a lesson in family values, Cell, 80:529-532 (1995).
The Complete blog for the preparation of pharmaceutical salts, Retrieved from the Internet: URL:http://kilomentor.chemicalblogs.com/55kilomentor/archive/552 the complete blog for the preparation of pharmaceutical.salts.html, 1-10 (2008).
Traenckner et al., A proteasome inhibitor prevents activation of NF-kappaB and stabilizes a newly phosphorylated form of IkappaB-alpha that is still bound to NF-kappaB, EMBO J., 13:5433-5441 (1994).
U.S. Appl. No. 17/066,556, Notice of Allowance, dated Jun. 21, 2022.
Wermuth, Newest Pharmaceutical Chemistry, vol. 2, Corp. TechnoMic, 347-365 (1999).
Yu et al., The ubiquitin-proteasome System facilitates the transfer of murine coronavirus from endosome to cytoplasm during virus entry, J. viral., 79(1):644-648 (2005).
European Patent Application No. 23191555.4, Extended European Search Report, dated Feb. 19, 2024.
Zhang et al., Design, synthesis and biological evaluation of novel tripeptidyl epoxyketone derivatives constructed from β-amino acid

(56) References Cited

OTHER PUBLICATIONS as proteasome inhibitors, Bioorganic & Medicinal Chemistry, 22: 2955-2965 (2014).

* cited by examiner

PROCESS OF PREPARING A PEPTIDE EPOXYKETONE IMMUNOPROTEASOME INHIBITOR, AND PRECURSORS THEREOF

BACKGROUND

Technical Field

The disclosure relates to methods and processes of preparing (2S,3R)—N-[(2S)-3-(cyclopent-1-en-1-yl)-1-[(2R)-2-methyloxiran-2-yl]-1-oxopropan-2-yl]-3-hydroxy-3-(4-methoxyphenyl)-2-[(2S)-2-[2-(morpholin-4-yl)acetamido]propanamido]propanamide, and precursors thereof.

Description of Related Technology

The compound, (2S,3R)—N-[(2S)-3-(cyclopent-1-en-1-yl)-1-[(2R)-2-methyloxiran-2-yl]-1-oxopropan-2-yl]-3-hydroxy-3-(4-methoxyphenyl)-2-[(2S)-2-[2-(morpholin-4-yl)acetamido]propanamido]propanamide ("compound G"), is useful as an immunoproteasome inhibitor:

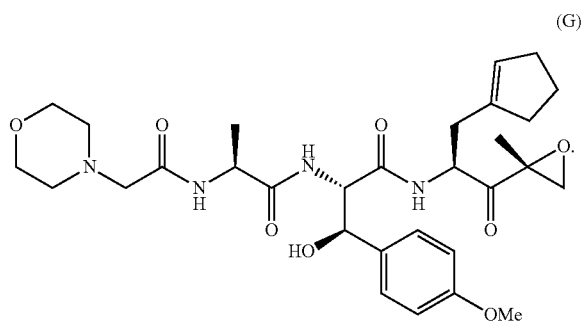 [SMILES: COc1ccc([C@@H](O)[C@H](NC(=O)[C@H](C)NC(=O)CN2CCOCC2)C(=O)N[C@@H](CC2=CCCC2)C(=O)[C@@]2(C)CO2)cc1]

(G)

In eukaryotes, protein degradation is predominately mediated through the ubiquitin pathway in which proteins targeted for destruction are ligated to the 76 amino acid polypeptide ubiquitin. Once targeted, ubiquitinated proteins then serve as substrates for the 26S proteasome, a multicatalytic protease, which cleaves proteins into short peptides through the action of its three major proteolytic activities. While having a general function in intracellular protein turnover, proteasome-mediated degradation also plays a key role in many processes such as major histocompatibility complex (MHC) class I antigen presentation, apoptosis, cell growth regulation, NF-κB activation, antigen processing, and transduction of pro-inflammatory signals.

The 20S proteasome is a 700 kDa cylindrical-shaped multicatalytic protease complex comprised of 28 subunits organized into four rings. In yeast and other eukaryotes, 7 different α subunits form the outer rings and 7 different β subunits comprise the inner rings. The α subunits serve as binding sites for the 19S (PA700) and 1 IS (PA28) regulatory complexes, as well as a physical barrier for the inner proteolytic chamber formed by the two β subunit rings. Thus, in vivo, the proteasome is believed to exist as a 26S particle ("the 26S proteasome"). In vivo experiments have shown that inhibition of the 20S form of the proteasome can be readily correlated to inhibition of 26S proteasome. Cleavage of amino-terminal prosequences of β subunits during particle formation expose amino-terminal threonine residues, which serve as the catalytic nucleophiles. The subunits responsible for catalytic activity in proteasomes thus possess an amino terminal nucleophilic residue, and these subunits belong to the family of N-terminal nucleophile (Ntn) hydrolases (where the nucleophilic N-terminal residue is, for example, Cys, Ser, Thr, and other nucleophilic moieties). This family includes, for example, penicillin G acylase (PGA), penicillin V acylase (PVA), glutamine PRPP amidotransferase (GAT), and bacterial glycosylasparaginase. In addition to the ubiquitously expressed β subunits, higher vertebrates also possess three interferon-y-inducible β subunits (LMP7, LMP2 and MECL1), which replace their normal counterparts, B5, B1 and B7 respectively, thus altering the catalytic activities of the proteasome. Through the use of different peptide substrates, three major proteolytic activities have been defined for the eukaryote 20S proteasome: chymotrypsin-like activity (CT-L), which cleaves after large hydrophobic residues; trypsin-like activity (T-L), which cleaves after basic residues; and peptidyl-glutamyl peptide hydrolyzing activity (PGPH), which cleaves after acidic residues. Two additional less characterized activities have also been ascribed to the proteasome: BrAAP activity, which cleaves after branched-chain amino acids; and SNAAP activity, which cleaves after small neutral amino acids. The major proteasome proteolytic activities appear to be contributed by different catalytic sites, since inhibitors, point mutations in R subunits and the exchange of γ interferon-inducing β subunits alter these activities to various degrees.

PCT publication no. WO 2014/152134, which is incorporated herein by reference, describes tripeptide epoxy immunoproteasome inhibitors, such as Compound G, and methods for their small-scale synthesis. However, a large-scale synthesis of tripeptide epoxy immunoproteasome inhibitors, such as Compound G, is needed for commercial development.

SUMMARY OF THE INVENTION

In one aspect, the disclosure provides a method of preparing (2S,3R)—N-[(2S)-3-(cyclopent-1-en-1-yl)-1-[(2R)-2-methyloxiran-2-yl]-1-oxopropan-2-yl]-3-hydroxy-3-(4-methoxyphenyl)-2-[(2S)-2-[2-(morpholin-4-yl)acetamido]propanamido]propanamide (compound "G")

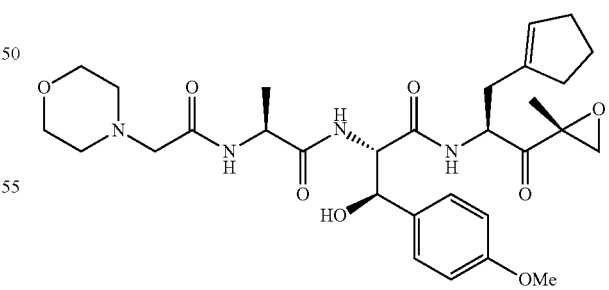

comprising:
(a) admixing a tertiary amine base and a suspension of:
(i) (2S,3R)-3-hydroxy-3-(4-methoxyphenyl)-2-((S)-2-(2-morpholino-acetamido)propanamido)propanoic acid (compound "E"):

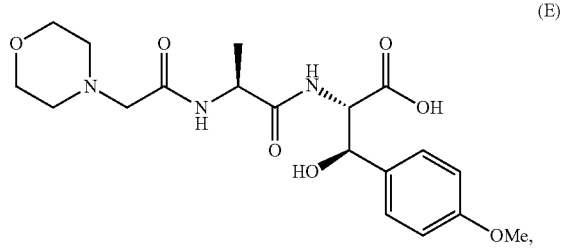 [SMILES: COc1ccc([C@@H](O)[C@H](NC(=O)[C@H](C)NC(=O)CN2CCOCC2)C(=O)O)cc1]

and (ii) (S)-3-(cyclopent-1-en-1-yl)-1-((R)-2-methyloxiran-2-yl)-1-oxopropan-2-aminium salt (compound "F"):

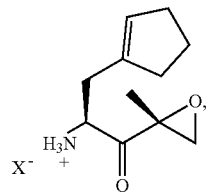

wherein X⁻ is a counterion;
in an aprotic solvent to form a mixture; and
(b) admixing a coupling agent and the mixture of step (a) to form compound G; wherein the temperature of each admixing step is maintained at −20° C. to 25° C.

In some embodiments, X⁻ is selected from the group consisting of tosylate, triflate, acetate, naphthalene sulfonate, 4-nitrobenzenesulfonate, sulfate, methylsulfate, nitrate, fluoride, chloride, bromide, and combinations thereof. In some cases, wherein X⁻ is tosylate, naphthalene sulfonate, or 4-nitrobenzenesulfonate. For example, X⁻ is tosylate.

In various embodiments, the aprotic solvent is selected from the group consisting of acetonitrile ("ACN"), dichloromethane ("DCM"), tetrahydrofuran ("THF"), dimethylacetamide ("DMAc"), ethyl acetate ("EtOAc"), isopropyl acetate ("iPrOAc"), dimethylformamide ("DMF"), and combinations thereof. For example, the aprotic solvent can be DCM.

In some cases, the tertiary amine base is selected from the group consisting of N,N-diisopropylethylamine ("DIPEA"), triethylamine ("TEA"), N-methylmorpholine ("NMM"), 2,2,6,6-tetramethylpiperidine ("TMP"), 2,4,6-trimethylpyridine ("collidine"), and combinations thereof. For example, the tertiary amine base can includes DIPEA. In various cases, the molar ratio of the tertiary amine base to compound E is in a range of 1:1 to 4:1.

In some embodiments, the coupling agent comprises a carbodiimide reagent, a phosphonium reagent, a uronium reagent, an immonium reagent, an imidazolium reagent, an organophosphorus reagent, an acid chloride reagent, a chloroformate reagent, or a pyridinium reagent. In various embodiments, the uronium reagent is selected from the group 1-[Bis(dimethylamino)methylene]-1H-1,2,3-triazolo[4,5-b]pyridinium 3-oxid hexafluorophosphate ("HATU"), O-(Benzotriazol-1-yl)-N,N,N',N'-tetramethyluronium hexafluorophosphate ("HBTU"), and combinations thereof. For example, the uronium reagent can be HATU. In some cases, the molar ratio of coupling agent to compound E is 1 to 1. The coupling reagent further comprises a coupling additive. In some embodiments, the coupling additive is selected from the group consisting of a benzotriazole, a dicarboximide, a succinimide, and combinations thereof. In various embodiments, the coupling additive is selected from the group consisting of N-hydroxysuccinimide ("HOSu"), N-hydroxy-5-norbornene-2,3-dicarboximide ("HONB"), 1-hydroxybenzotriazole ("HOBt"), 6-chloro-1-hydroxybenzotriazole ("Cl-HOBt"), 1-hydroxy-7-azabenzotriazole ("HOAt"), and combinations thereof.

In various cases, the temperature of each admixing step is maintained at −15° C. to 25° C. In some cases, the admixing of step (a) comprises stirring the mixture for up to 10 minutes. In various embodiments, the admixing of step (b) comprises stirring for up to two hours. In some embodiments, compound G is washed with one or more of the following: water, potassium phosphate monobasic, sodium bicarbonate, and sodium sulfate.

In various embodiments, compound E is prepared by admixing a reductant and benzyl (2S,3R)-3-hydroxy-3-(4-methoxyphenyl)-2-((S)-2-(2-morpholinoacetamido)propanamido)propanoate (compound "D")

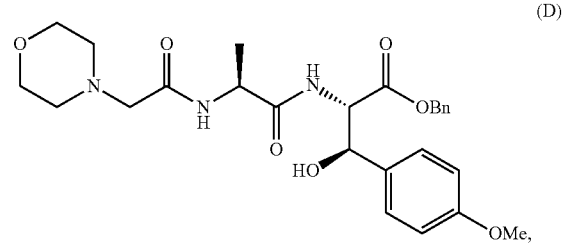 [SMILES: COc1ccc([C@@H](O)[C@H](NC(=O)[C@H](C)NC(=O)CN2CCOCC2)C(=O)OCc2ccccc2)cc1]

to form compound E. In some cases, the reductant is selected from the group consisting of H₂, Pd/C; H₂, Pd(OH)₂/C; Li; Na; lithium 4,4'-di-tert-butylbiphenyl ("Li DTBBP"), and combinations thereof. In some embodiments, the admixing of the reductant and compound D occurs under a nitrogen atmosphere. The admixing of the reductant and compound D can occur for up to 4 hours. Further, the admixing can occur at a temperature in a range of 10° C. to 20° C. In various cases, the preparation of compound E further includes one or more of the following: filtering compound E across diatomite; washing compound E; and crystallizing compound E with THF and water.

Another aspect of the disclosure provides a method of preparing (S)-3-(cyclopent-1-en-1-yl)-1-((R)-2-methyloxiran-2-yl)-1-oxopropan-2-aminium salt (compound "F")

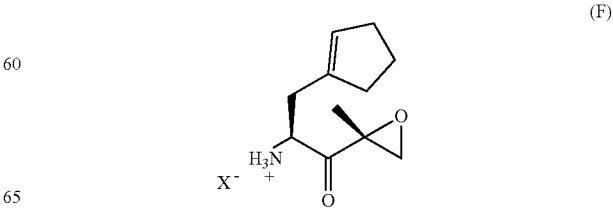

comprising:

(a) admixing trifluoroacetic acid ("TFA") and tert-butyl-((S)-3-(cyclopent-1-en-1-yl)-1-((R)-2-methyloxiran-2-yl)-1-oxopropan-2-yl)carbamate (compound "H"):

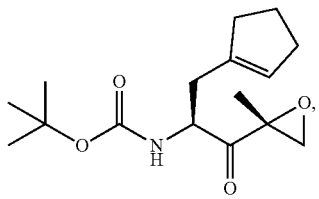

(H)

in an aprotic solvent at a temperature in a range of −5° C. to 5° C. to form a mixture;

(b) concentrating the mixture; and (c) admixing an acid and the concentrated mixture of step (b) at a temperature in a range of −5° C. to 5° C. to form compound F, wherein X⁻ is a conjugate base of the acid.

In some embodiments, the acid is selected from the group consisting of p-toluenesulfonic acid, trifluoromethanesulfonic acid, acetic acid, trifluoroacetic acid, naphthalene sulfonic acid, 4-nitrobenzenesulfonic acid, sulfonic acid, methylsulfonic acid, benzenesulfonic acid, nitric acid, HF, HCl, HBr, and combinations thereof. For example, the acid can be selected from the group consisting of toluenesulfonic acid, naphthalene sulfonic acid, 4-nitrobenzenesulfonic acid, and combinations thereof. In some cases, the molar ratio of the acid to compound H is 1 to 1. In various cases, the molar ratio of TFA to compound H is 8 to 1. In various embodiments, the aprotic solvent in step (a) is selected from the group consisting of acetonitrile ("ACN"), dichloromethane ("DCM"), tetrahydrofuran ("THF"), dimethylacetamide ("DMAc"), methyl tert-butyl ether ("MTBE"), isopropyl ether ("IPE"), and combinations thereof. For example, the aprotic solvent can include DCM. In some cases, the temperature in step (a), step (c), or both is 0° C. In various cases, the mixture of step (b) is concentrated at a temperature in a range of 15° C. to 25° C. In various embodiments, the admixing of step (a) comprises stirring for 2 hours. In some cases, the admixing of step (c) comprises stirring for 10 to 12 hours. In some embodiments, the concentrated mixture of step (b) is further washed with a polar, aprotic solvent at a temperature in a range of 15° C. to 25° C. Suitable polar, aprotic solvents include diethyl ether, tetrahydrofuran ("THF"), acetonitrile ("ACN"), methyl tert-butyl ether ("MBTE"), isopropyl ether ("IPE") and combinations thereof. For example, the polar, aprotic solvent can include MBTE. In some cases, the method further includes one or more of the following steps: filtering compound F, washing compound F with a polar, aprotic solvent, and drying compound F. The polar, aprotic solvent for washing compound F can be selected from the group consisting of diethyl ether, tetrahydrofuran ("THF"), acetonitrile ("ACN"), methyl tert-butyl ether ("MBTE"), isopropyl ether ("IPE"), and combinations thereof.

Yet another aspect of the disclosure provides a method of preparing benzyl (2S,3R)-3-hydroxy-3-(4-methoxyphenyl)-2-((S)-2-(2-morpholinoacetamido)propanamido)propanoate (compound "D")

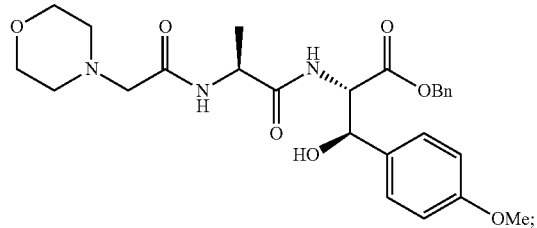

(D)

comprising:

(a) admixing a tertiary amine base and a suspension of:
(i) (2S,3R)-1-(benzyloxy)-3-hydroxy-3-(4-methoxyphenyl)-1-oxopropan-2-aminium salt (compound "B"):

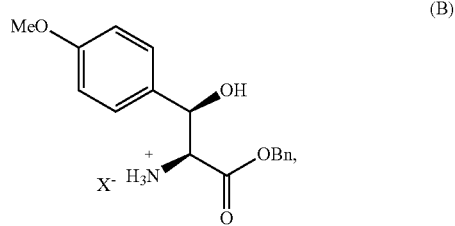

(B)

wherein X⁻ is a counterion; and
(ii) (2-morpholinoacetyl)-L-alanine (compound "C"):

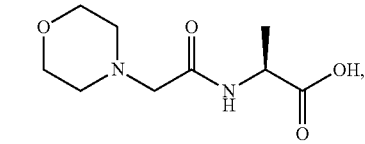

(C)

in an aprotic solvent to form a mixture; and
(b) admixing a coupling agent and the mixture of step (a) to form compound D;
wherein the temperature of each admixing step is maintained at −5° C. to 5° C.

In some embodiments, X⁻ is selected from the group consisting of tosylate, triflate, acetate, naphthalene sulfonate, 4-nitrobenzenesulfonate, sulfate, methylsulfate, nitrate, fluoride, chloride, bromide, and combinations thereof. For example, X⁻ can be chloride. In some cases, the aprotic solvent is selected from the group consisting of acetonitrile ("ACN"), dichloromethane ("DCM"), tetrahydrofuran ("THF"), dimethylacetamide ("DMAc"), and combinations thereof. For example, the aprotic solvent can include ACN. In various embodiments, the tertiary amine base is selected from the group consisting of N,N-diisopropylethylamine ("DIPEA"), triethylamine ("TEA"), N-methylmorpholine ("NMM"), 2,2,6,6-tetramethylpiperidine ("TMP"), 2,4,6-trimethylpyridine ("collidine"), and combinations thereof. For example, the tertiary amine base can include DIPEA. In various cases, the coupling agent comprises a carbodiimide reagent, a phosphonium reagent, a uronium reagent, an immonium reagent, an imidazolium reagent, an organophosphorus reagent, an acid chloride reagent, a chloroformate reagent, or a pyridinium reagent. In some embodiments, the uronium reagent is selected from the group 1-[Bis(dimethylamino)methylene]-1H-1,2,3-triazolo[4,5-b]pyridinium 3-oxid hexafluorophosphate ("HATU"), O-(Benzotriazol-1-yl)-N,N,N',N'-tetramethyluronium hexafluorophosphate ("HBTU"), and combinations thereof. For example, the uronium reagent can include HATU. In some embodiments, the molar ratio of coupling agent to compound B is 1 to 1. In various embodiments, the coupling reagent further includes a coupling additive. The coupling additive can be selected from the group consisting of a benzotriazole, a dicarboximide, a succinimide, and combinations thereof. For example, the coupling reagent can be selected from the group consisting of N-hydroxysuccinimide ("HOSu"), N-hydroxy-5-norbornene-2,3-dicarboximide ("HONB"), 1-hydroxybenzotriazole ("HOBt"), 6-chloro-1-hydroxybenzotriazole ("Cl-HOBt"), 1-hydroxy-7-azabenzotriazole ("HOAt"), and combinations thereof. In some cases, the temperature of each admixing step is maintained at −5° C. to 5° C. In some embodiments, the admixing of step (b) comprises mixing portions of the coupling agent with the mixture from step (a) over 30 minutes. In various cases, the admixing of step (b) comprises stirring 2 hours. In some embodiments, the method further includes washing compound D with one or more of the following: water, isopropyl acetate, potassium phosphate monobasic, sodium bicarbonate, sodium sulfate, and THF.

Compound B can be prepared by admixing (i) an acid and (ii) benzyl (2S,3R)-2-((tert-butoxycarbonyl)amino)-3-hydroxy-3-(4-methoxyphenyl)propanoate (compound "A"):

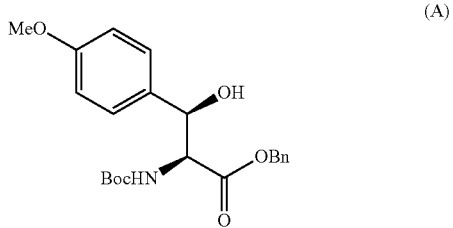 [SMILES: COc1ccc([C@@H](O)[C@H](NC(=O)OC(C)(C)C)C(=O)OCc2ccccc2)cc1]

(A)

in a polar, aprotic solvent, to form compound B. In some embodiments, the acid is selected from the group consisting of p-toluenesulfonic acid, trifluoromethanesulfonic acid, acetic acid, trifluoroacetic acid, naphthalene sulfonic acid, 4-nitrobenzenesulfonic acid, sulfonic acid, methylsulfonic acid, nitric acid, HF, HCl, HBr, and combinations thereof. For example, the acid can include trifluoroacetic acid or HCl. In some embodiments, the polar, aprotic solvent is selected from the group consisting of ethyl acetate, N-methylpyrrolidone ("NMP"), tetrahydrofuran ("THF"), acetone, dimethylformamide ("DMF"), acetonitrile ("ACN"), dimethyl sulfoxide ("DMSO"), dicholormethane ("DCM"), and combinations thereof. For example, the polar, aprotic solvent can include ethyl acetate, DCM, or combinations thereof. In some cases, the admixing step includes stirring at a temperature in a range of 15° C. to 25° C. The method can further include filtering compound B, drying compound B, or both.

Another aspect of the disclosure provides a crystalline form of (2S,3R)-1-(benzyloxy)-3-hydroxy-3-(4-methoxyphenyl)-1-oxopropan-2-aminium chloride salt (compound "B-Cl")

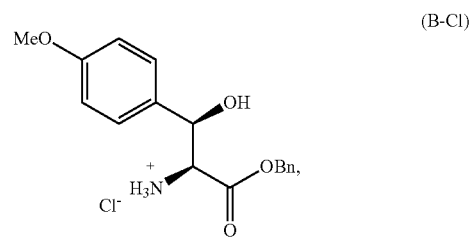 [SMILES: COc1ccc([C@@H](O)[C@H](N)C(=O)OCc2ccccc2)cc1 ; [Cl-]]

(B-Cl)

characterized by an X-ray powder diffraction pattern comprising peaks at 4.6, 9.2, 13.8, 18.5, and 32.9±0.2° 2θ using Cu Kα radiation.

Yet another aspect of the disclosure provides a crystalline form of (2S,3R)-3-hydroxy-3-(4-methoxyphenyl)-2-((S)-2-(2-morpholinoacetamido)propanamido)propanoic acid (compound "E"):

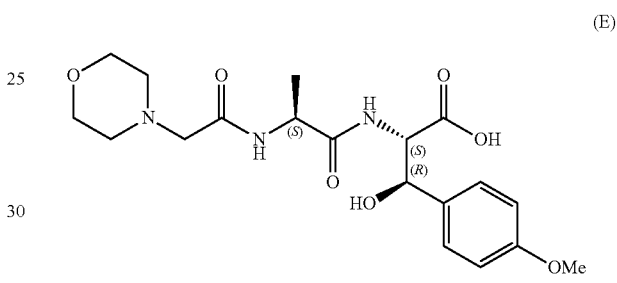

(E)

characterized by an X-ray powder diffraction pattern comprising peaks at 6.2, 8.5, 9.7, 12.7, 13.7, 16.0, 16.9 17.2, 18.4, 18.9, 19.2, 19.7, 22.5, 24.7, 25.4, 28.7, and 29.7±0.2° 2θ using Cu Kα radiation.

Still another aspect of the disclosure provides a crystalline form of (S)-3-(cyclopent-1-en-1-yl)-1-((R)-2-methyloxiran-2-yl)-1-oxopropan-2-aminium salt (compound "F"):

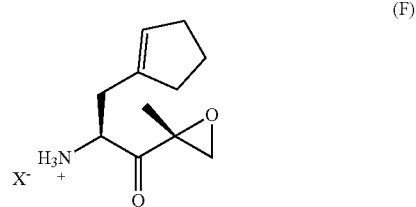

(F)

wherein X⁻ is tosylate, characterized by an X-ray powder diffraction pattern comprising peaks at 6.8, 7.1, 7.4, 14.2, 14.8, 17.0, 17.5, 17.8, 18.5, 18.7, 20.1, 20.3, 23.0, 23.6, 24.5, 29.3, and 31.2±0.2° 2θ using Cu Kα radiation.

Further aspects and advantages will be apparent to those of ordinary skill in the art from a review of the following detailed description. While the methods disclosed herein are susceptible of embodiments in various forms, the description hereafter includes specific embodiments with the understanding that the disclosure is illustrative, and is not intended to limit the invention to the specific embodiments described herein.

DETAILED DESCRIPTION

Figure 1:
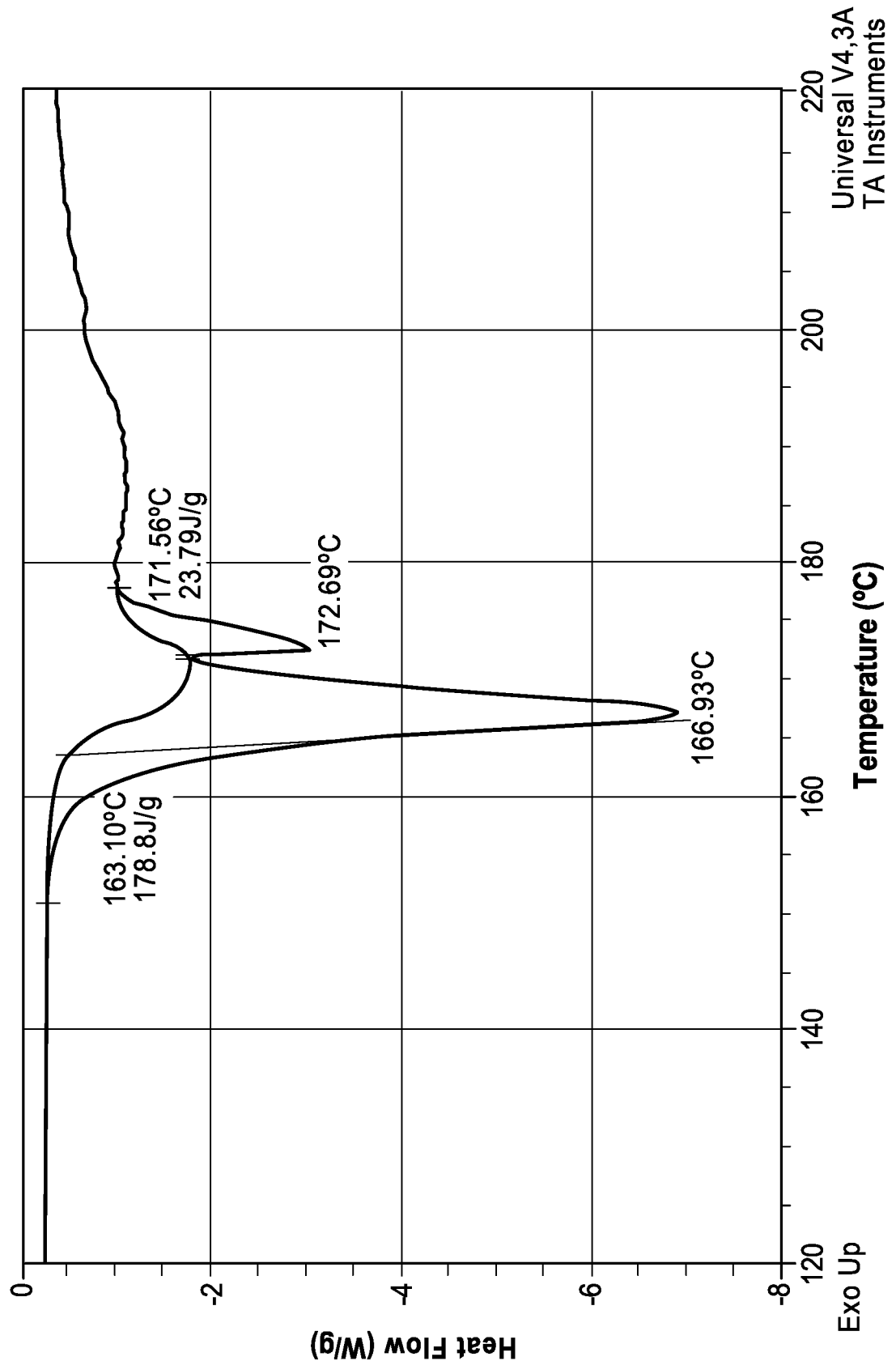
FIG. 1 depicts the characteristic differential scanning calorimetry ("DSC") curve for (2S,3R)-1-(benzyloxy)-3-hydroxy-3-(4-methoxyphenyl)-1-oxopropan-2-aminium salt (compound "B").

Disclosed herein is a process for the preparation of (2S,3R)—N-[(2S)-3-(cyclopent-1-en-1-yl)-1-[(2R)-2-methyloxiran-2-yl]-1-oxopropan-2-yl]-3-hydroxy-3-(4-methoxyphenyl)-2-[(2S)-2-[2-(morpholin-4-yl)acetamido]propanamido]propanamide (compound "G"):

(G)

and precursors thereof, and in some cases, the process is for large-scale preparation of compound G. The overall scheme for the preparation of compound G is shown in Scheme 1, below.

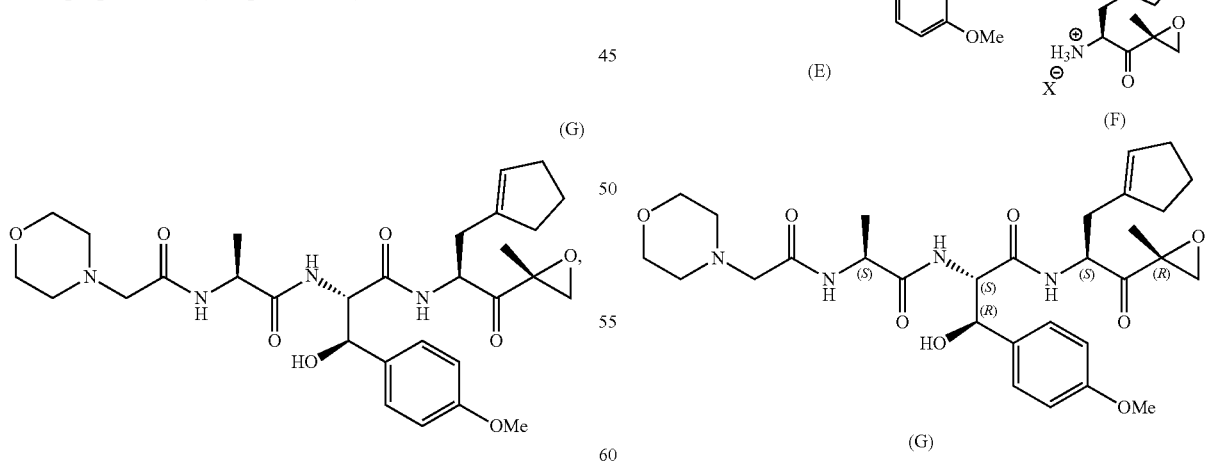

Scheme 1.

The optical purity of compound G is controlled during the synthesis by the quality of the starting materials and the specific reagents used for the transformations.

The compounds disclosed herein may be identified either by their chemical structure and/or chemical name herein.

When the chemical structure and chemical name conflict, the chemical structure is determinative of the identity of the compound.

Unless otherwise indicated, terms and abbreviations used in this specification include the normal and customary meaning to those in the relevant field.

As the present disclosure's contribution is not limited to particular embodiments or aspects disclosed herein, the disclosure provides to one of ordinary skill in the art additional embodiments including changes and modifications to adapt to various usages and conditions. For example, changes and modifications to materials, methods of synthesis, or procedures described herein will be apparent to one of ordinary skill.

When ranges are used herein for physical properties, such as molecular weight, or chemical properties, such as chemical formulae, all combinations and subcombinations of ranges and specific embodiments therein are intended to be included.

Preparation of Compound G

In one aspect, provided herein is a method for preparing compound G. Compound G can be prepared in two steps-step (a) and step (b). In step (a), a mixture is formed by admixing together a tertiary amine base and a suspension that includes: (i) (2S,3R)-3-hydroxy-3-(4-methoxyphenyl)-2-((S)-2-(2-morpholino-acetamido)propanamido)propanoic acid (compound "E"):

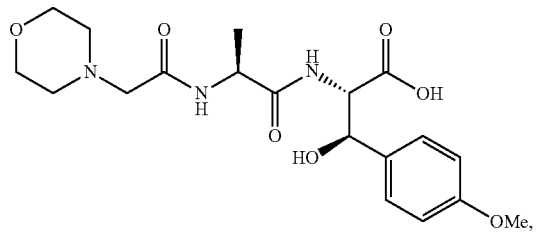

(E)

and (ii) (S)-3-(cyclopent-1-en-1-yl)-1-((R)-2-methyloxiran-2-yl)-1-oxopropan-2-aminium salt (compound "F"):

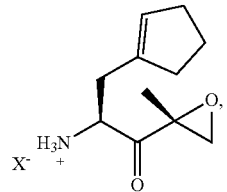

(F)

wherein X⁻ is a counterion, in an aprotic solvent to form a mixture. In step (b), the mixture from step (a) and a coupling agent are admixed together at a temperature in a range of about −20° C. to about 25° C. to form compound G.

The counterion (X⁻) can be any anion capable of forming an ionic bond with the ammonium group of compound F. In some embodiments, X⁻ is selected from the group consisting of tosylate, triflate, acetate, naphthalene sulfonate, 4-nitrobenzenesulfonate, sulfate, methylsulfate, nitrate, fluoride, chloride, bromide, and combinations thereof. In some cases, X⁻ can be tosylate, naphthalene sulfonate, or 4-nitrobenzenesulfonate. For example, X⁻ can be tosylate.

The aprotic solvent can be any aprotic solvent (or mixture of solvents) in which the nucleophilic acyl substitution reaction between compounds E and F can proceed. Suitable aprotic solvents include acetonitrile ("ACN"), dichloromethane ("DCM"), tetrahydrofuran ("THF"), dimethylacetamide ("DMAc"), ethyl acetate ("EtOAc"), isopropyl acetate ("iPrOAc"), dimethylformamide ("DMF"), and combinations thereof. In various embodiments, the aprotic solvent is selected from the group consisting of ACN, THF, DMF, and DCM. For example, the aprotic solvent can include DCM.

Compound E and compound F can be present in a molar ratio of about 0.8:1 to 1.3:1. In some embodiments, compounds E and F are present in a ratio of about 0.9:1 to 1.1:1. For example, the molar ratio of compounds E and F can be about 1:1, or in a range of 1:1.11 to 1:1.15.

The tertiary amine base can be any tertiary amine base that can promote or catalyze the nucleophilic acyl substitution reaction between compounds E and F. Suitable tertiary amine bases can include, for example, N,N-diisopropylethylamine ("DIPEA"), triethylamine ("TEA"), N-methylmorpholine ("NMM"), 2,2,6,6-tetramethylpiperidine ("TMP"), 2,4,6-trimethylpyridine ("collidine"), and combinations thereof. For example, the tertiary amine base can include DIPEA. The tertiary amine base can be present in a molar ratio to compound E in a range of about 1:1 to about 4:1. In some embodiments, the tertiary amine base and compound E are present in a ratio of about 2.5:1 to 4:1 or 2.5:1 to 3.5:1. For example, the ratio of tertiary amine base to compound E can be about 3.5:1 or 3.9:1.

The coupling agent can include, for example, a carbodiimide reagent, a phosphonium reagent, a uronium reagent, an immonium reagent, an imidazolium reagent, an organophosphorus reagent, an acid chloride reagent, a chloroformate reagent, a pyridinium reagent, or combinations thereof. See, e.g., Han & Kim, Tetrahedron Report 60:2447-2467 (2004); Montalbetti and Falque, Tetrahedron 61:10827-10852 (2005). The carbodiimide can include, for example, N,N'dicyclohexylcarbodiimide ("DCC"), 1,3-diisopropylcarbodiimide ("DIC"), 1-ethyl-3-(3-dimethylaminopropyl)carbodiimide ("EDC"), or and isopropylcarbodiimide ("CIC"), and combinations thereof. The phosphonium agent can include, for example, (benzotriazol-1-yloxy)tris(dimethylamino)phosphonium hexafluorophosphate ("BOP") or benzotriazol-1-yl-oxytripyrrolidinophosphonium hexafluorophosphate ("PyBOP"), and combinations thereof. The uronium agent can include, for example, 1-[Bis(dimethylamino)methylene]-1H-1,2,3-triazolo[4,5-b]pyridinium 3-oxid hexafluorophosphate ("HATU"), O-(Benzotriazol-1-yl)-N,N,N',N-tetramethyluronium hexafluorophosphate ("HBTU"), and combinations thereof. For example, the uranium agent can include HATU. The imidazolium agent can include, for example, 1,1'-carbonyldiimidazole ("CDI"). The acid chloride agent include, for example, pivaloyl chloride, 2, 4, 6-trimethylbenzoyl chloride, and combinations thereof. The chloroformate agent can include, for example, ethyl chloroformate, isobutyl chloroformate, and combinations thereof. The coupling agent can be present in a molar ratio to compound E in a range of about 0.8:1 to about 1:5. In some embodiments, the coupling agent and compound E are present in a ratio of about 0.9:1 to 1.1:1. For example, the ratio of the coupling agent to compound E can be about 1:1 or 1.11:1.

The coupling reaction can be performed in the presence of a coupling additive. Coupling additives are known in the art and any suitable one can be used for the formation of compound G. Suitable coupling additives include, for example, benzotriazoles, dicarboximides, and succinimides. In some embodiments, the coupling additives is selected from the group consisting of N-hydroxysuccinimide ("HOSu"), N-hydroxy-5-norbornene-2,3-dicarboximide ("HONB"), 1-hydroxybenzotriazole ("HOBt"), 6-chloro-1-hydroxybenzotriazole ("Cl-HOBt"), 1-hydroxy-7-azabenzotriazole ("HOAt"), and combinations thereof. For example, the coupling additive can include HOBt.

The temperature of each admixing step is maintained in a range of about −20° C. to about 25° C. In some embodiments, the temperature of each admixing step is maintained in a range of about −15° C. to about 25° C. In some cases, the temperature of each admixing step is maintained in a range of about −5° C. to about 15° C. For example, the temperature of each admixing step can be maintained in a range of about −5° C. to about 5° C. The temperature of each admixing step can be the same or different.

In step (a) of the preparation of compound G, the admixing can occur for a time period of up to about 30 minutes (e.g., up to about 5, 6, 7, 8, 9, 10, 11, 12, 13, 14, 15, 16, 16, 18, 19, 20, 21, 22, 23, 24, 25, 26, 27, 28, 29, or 30 minutes). In some embodiments, the admixing of step (a) can occur for up to about 10 minutes. In some cases, the admixing of step (a) can occur for at least about 30 seconds or at least about 1 minute (e.g., at least about 2, 3, 4, 5, 6, 7, 8 or 9 minutes). For example, the admixing of step (a) can occur for about 30 seconds to about 30 minutes, or for about 1 minute to about 20 minutes, or for about 2 minutes to about 15 minutes, or for about 5 minutes to about 10 minutes.

In step (b) of the preparation of compound G, the admixing can occur for a time period of up to about 3 hours (e.g., up to about 1, 1.5, 2, 2.5, or 3 hours). In some embodiments, the admixing of step (b) can occur for up to about 2 hours. In some cases, the admixing of step (b) can occur for at least about 30 minutes, or at least about 1 hour, or at least about 1.5 hours. For example, the admixing of step (b) can occur for about 30 minutes to about 3 hours, or for about 30 minutes to about 2.5 hours, or for about 1 hour to about 2 hours.

In step (b), the coupling reaction can occur under a nitrogen atmosphere. In some cases, the coupling reaction does not occur under a nitrogen atmosphere.

After step (b), compound G can be washed with one or more solvents. The temperature during washing can optionally be in a range of about 0° to about 25° C., or about 15° C. to about 25° C. Suitable solvents for washing include, for example, water, potassium phosphate monobasic, sodium bicarbonate, sodium sulfate, and combinations thereof. In some embodiments, water is added to compound G after step (b), and the resulting biphasic mixture is separated into an aqueous layer and an organic layer before washing. In various cases, compound G can be washed with each of water, potassium phosphate monobasic, sodium bicarbonate, and sodium sulfate.

For example, compound G can be prepared by (a) admixing together compound E and compound F (1:1 molar ratio) in DCM for a time period of up to about 10 minutes to form a mixture, and (b) admixing the mixture from step (a) and about 1 molar equivalent of HATU for up to about two hours under a nitrogen atmosphere, wherein the temperature of each step is in a range of about −20° C. to about 25° C., or about −20° C. to 0° C. The resulting mixture can be quenched with water to result in a biphasic mixture. The organic layer can be separated, washed with water, then with potassium phosphate monobasic, followed by sodium bicarbonate and sodium sulfate (sequentially).

Preparation of Compound E

Compound E can be prepared by admixing a reductant and benzyl (2S,3R)-3-hydroxy-3-(4-methoxyphenyl)-2-((S)-2-(2-morpholinoacetamido)propanamido)propanoate (compound "D")

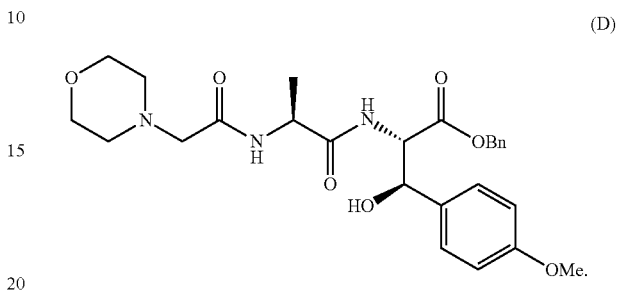

The reductant can be any suitable agent capable of removing the benzyl group on compound D to form the carboxylic acid of compound E. Suitable reductants include, for example, $H_2$, in the presence of Pd/C or Pd(OH)$_2$/C; Li; Na; lithium 4,4'-di-tert-butylbiphenyl ("Li DTBBP"), and combinations thereof. For example, the reductant can be $H_2$, in the presence of Pd/C.

The admixing of the reductant and compound D can occur in any solvent capable of allowing the reduction reaction to occur. For example, the solvent can include THF, methanol, or a combination thereof.

In some embodiments, compound D is provided under a nitrogen atmosphere prior to exposure to a hydrogen atmosphere. In various embodiments, the hydrogen atmosphere is established at about 15 psi.

The admixing of the reductant and compound D can occur for a time period of at least 30 minutes and up to about 5 hours (e.g., up to about 2, 2.5, 3, 3.5, 4, or 4.5 hours). In some embodiments, the admixing can occur for up to about 4 hours. In some cases, the admixing of the reductant and compound D can occur for at least about 30 minutes, or at least about 1 hour (e.g., at least about 1.5, or 2, or 2.5, or 3, or 3.5 hours). For example, the admixing can occur for about 30 minutes to about 5 hours, or about 1 hour to about 4 hours, or about 2 hour to about 4 hours.

The temperature of the admixing is maintained in a range of about 10° C. to about 20° C. In some embodiments, the temperature is maintained at about 17° C.

In some cases, after completion of the admixing, compound E is filtered, such as through diatomaceous earth (i.e., diatomite). The resulting filtrate can be subsequently washed with a suitable solvent (e.g., water, methanol, water, and combinations thereof).

Figure 2:
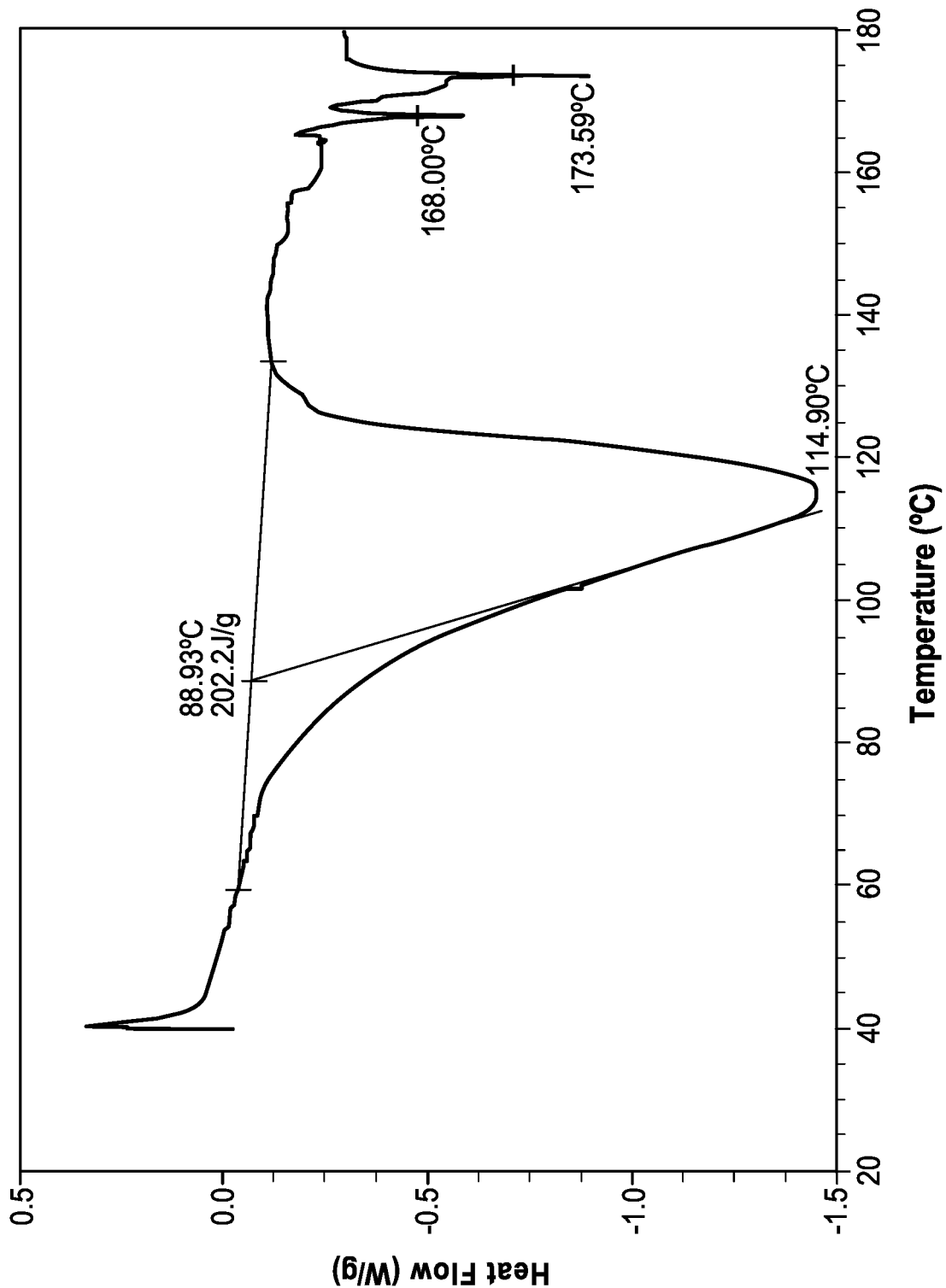
FIG. 2 depicts the characteristic DSC thermogram for (2S,3R)-3-hydroxy-3-(4-methoxyphenyl)-2-((S)-2-(2-morpholino-acetamido)propanamido)propanoic acid (compound "E").
Figure 3:
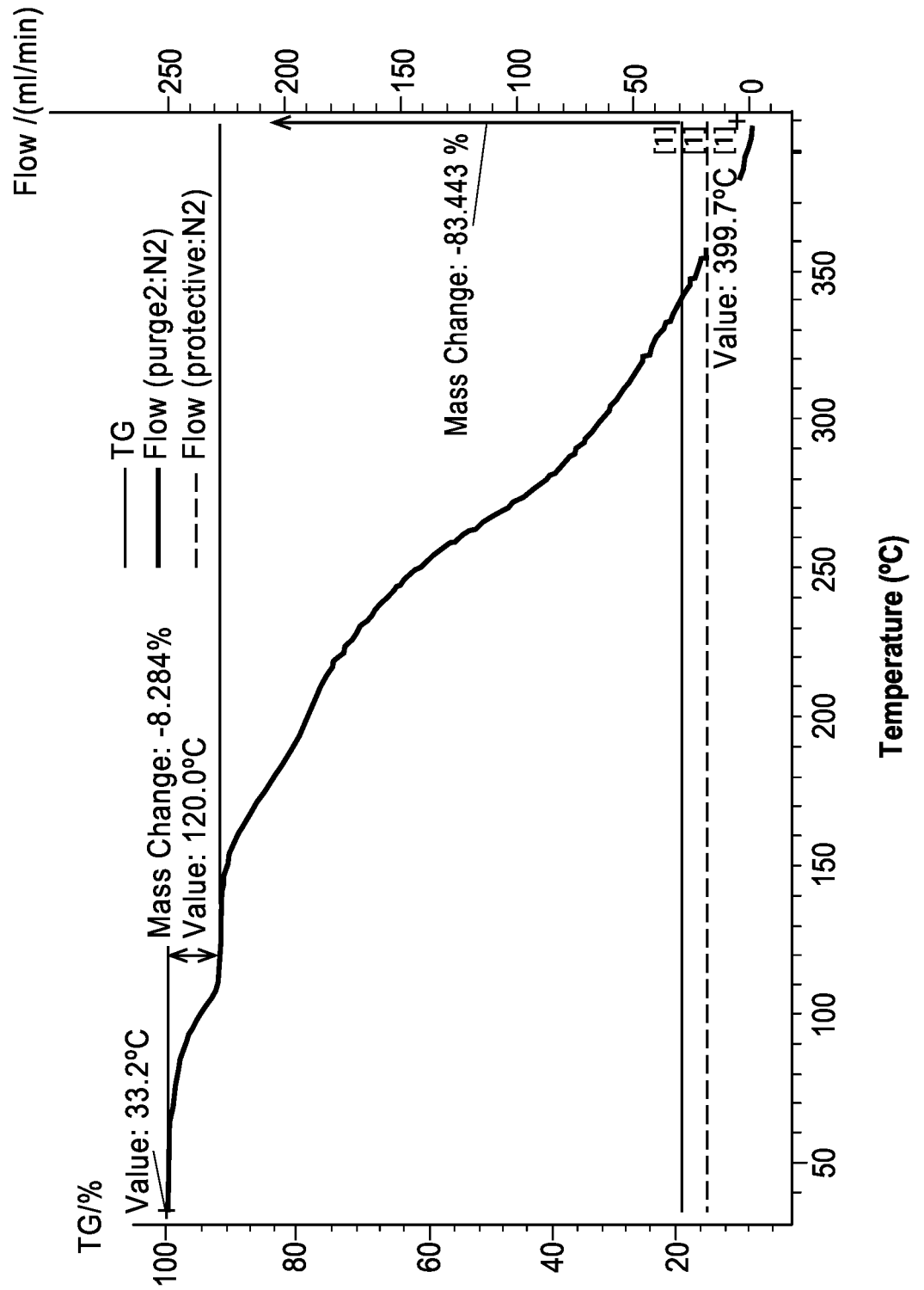
FIG. 3 depicts the characteristic thermogravimetric analysis ("TGA") data for compound E.
Figure 4:
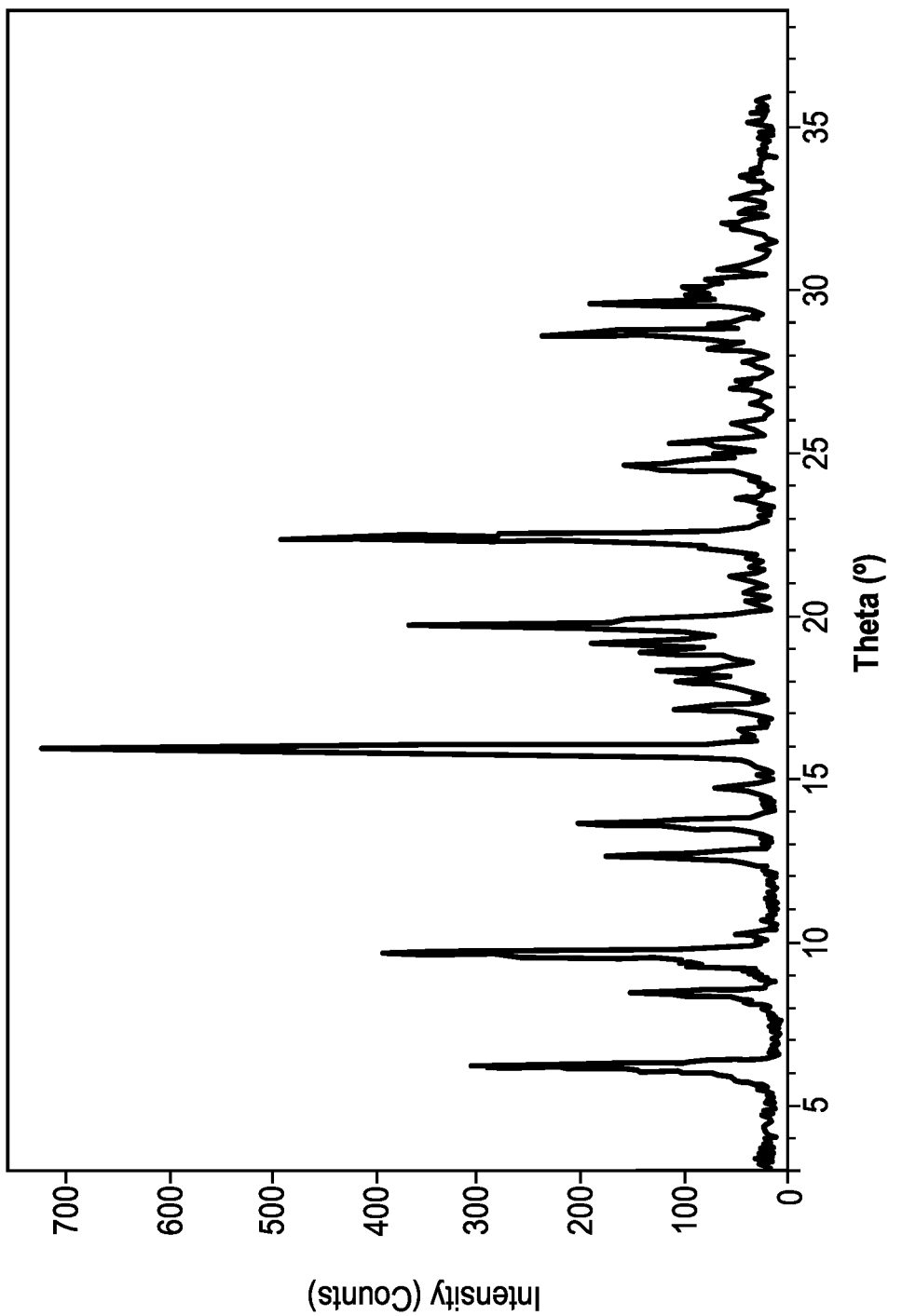
FIG. 4 depicts the characteristic X-ray powder diffraction pattern ("XRPD") for compound E.

Compound E (with or without washing) can be crystallized to form a polymorph, characterized by the differential scanning calorimetry ("DSC") thermogram, thermogravimetric analysis ("TGA") data, and X-ray power diffraction ("XRPD") pattern depicted in FIGS. 2, 3, and 4, respectively. For example, the crystallization of compound E can occur in THF and water by heating compound E to a temperature in a range of about 50° C. to about 70° C., or about 60° C. to about 70° C., or about 55° C. to about 65° C., and then cooling the temperature to about 0° C. Thus, another aspect of the present disclosure is a crystalline form of compound E, which is characterized by an XRPD pattern comprising peaks at 6.2, 8.5, 9.7, 12.7, 13.7, 16.0, 16.9 17.2, 18.4, 18.9, 19.2, 19.7, 22.5, 24.7, 25.4, 28.7, and 29.7±0.2° 2θ using Cu Kα radiation, as shown in FIG. 4.

For example, compound E can be prepared by admixing together a reductant, such as H₂, in the presence of Pd/C, and compound D under a nitrogen atmosphere, at 10° C. to 20° C., for a time period of at least 30 minutes up to 4 hours. Compound E can be filtered across diatomite, and the resulting filter cake can be washed (e.g., with water, methanol, and/or THF). Compound E can be crystallized by heating it to about 60° C. to 70° C., adjusting the temperature to about 55° C. to 65° C. and adding THE to mixture, heating the mixture back to 60° C. to 70° C., adding water to the heated mixture, cooling the mixture back to 55° C. to 65° C., adding a seed crystal to the mixture, and stirring the seeded mixture for about two hours at 0° C. Filtering, washing, and drying the cooled mixture results in crystalized compound E.

Preparation of Compound F

In another aspect, provided herein is a method of preparing compound F.

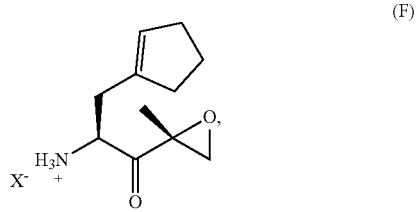

(F)

wherein X⁻ is a counterion.

Compound F can be prepared in three steps-steps (a), (b), and (c). In step (a), a mixture is formed by admixing together an aprotic solvent, trifluoroacetic acid ("TFA"), and tert-butyl-((S)-3-(cyclopent-1-en-1-yl)-1-((R)-2-methyloxiran-2-yl)-1-oxopropan-2-yl)carbamate (compound H):

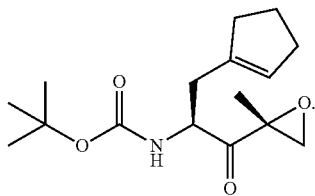

(H)

at a temperature in a range of about –5° C. to about 5° C. In step (b), the mixture from step (a) is concentrated. In step (c), the concentrated mixture of step (b) is admixed together with an acid at a temperature in a range of about –5° C. to 5° C. to form compound F.

The acid can be any acid capable of forming a salt with the amninium group of compound F. Suitable acids include, for example, p-toluenesulfonic acid, trifluoromethanesulfonic acid, acetic acid, trifluoroacetic acid, naphthalene sulfonic acid, 4-nitrobenzenesulfonic acid, sulfonic acid, methylsulfonic acid, benzenesulfonic acid, nitric acid, HF, HCl, HBr, and combinations thereof. In some embodiments, the acid is selected from the group consisting of p-toluenesulfonic acid, naphthalene sulfonic acid, 4-nitrobenzenesulfonic acid, and combinations thereof. For example, the acid can include p-toluenesulfonic acid.

The aprotic solvent in step (a) can be any aprotic solvent (or mixture of solvents) in which the reaction can proceed. Suitable aprotic solvents can include acetonitrile ("ACN"), dichloromethane ("DCM"), tetrahydrofuran ("THF"), dimethylacetamide ("DMAc"), methyl tert-butyl ether ("MTBE"), isopropyl ether ("IPE"), and combinations thereof. For example, the aprotic solvent can include DCM.

The trifluoroacetic acid in step (a) can be present in a molar ratio to compound H in a range of about 15:1 to 5:1. In some embodiments, the trifluoroacetic acid and Compound H are present in a ratio of about 10:1 to 7.5:1. For example, the molar ratio of trifluoroacetic acid and compound H can be about 8:1.

In some embodiments, the deprotection reaction of step (a) occurs under a nitrogen atmosphere.

The temperature of the mixture in step (a), step (c), or both step (a) and step (c) is maintained in a range of about –5° C. to about 5° C., or at about 0° C. In some embodiments, the mixture is concentrated in step (b) at a temperature in a range of about 15° C. to about 25° C.

In some cases, the admixing of step (a) can occur for a time period of at least 30 minutes up to about 3 hours (e.g., up to about 1, 1.5, 2, 2.5, or 3 hours). In some embodiments, the admixing of step (a) can occur for a time period of up to about 2 hours. In some cases, the admixing of step (a) can occur for at least about 30 minutes, or at least about 1 hour, or at least about 1.5 hours. For example, the admixing of step (a) can occur for about 30 minutes to about 3 hours, or about 30 minutes to about 2.5 hours, or about 1 hour to about 2 hours.

In various cases, the admixing of step (c) can occur for a time period of at least 5 hours up to about 12 hours (e.g., up to about 7, 8, 9, 10, or 11 hours). In some embodiments, the admixing of step (c) can occur for a time period of up to about 10 to 12 hours. In some cases, the admixing of step (c) can occur for at least about 5 hours (e.g., at least about 6, 7, 8, 9, or 10 hours). For example, the admixing of step (c) can occur for about 5 hours to about 12 hours, or about 10 hours to about 12 hours.

In some cases, the concentrated mixture of step (b) can be rinsed with a polar, aprotic solvent. Suitable polar, aprotic solvents include, for example, diethyl ether, tetrahydrofuran ("THF"), acetonitrile ("ACN"), methyl tert-butyl ether ("MBTE"), isopropyl ether ("IPE") and combinations thereof. For example, the polar, aprotic solvent can be MBTE.

After step (c), compound F can optionally be filtered at a temperature in a range of about –5° C. to about 5° C., washed with one or more polar, aprotic, solvents (e.g., diethyl ether, tetrahydrofuran ("THF"), acetonitrile ("ACN"), methyl tert-butyl ether ("MBTE"), isopropyl ether ("IPE"), and combinations thereof), and/or dried.

Figure 7:
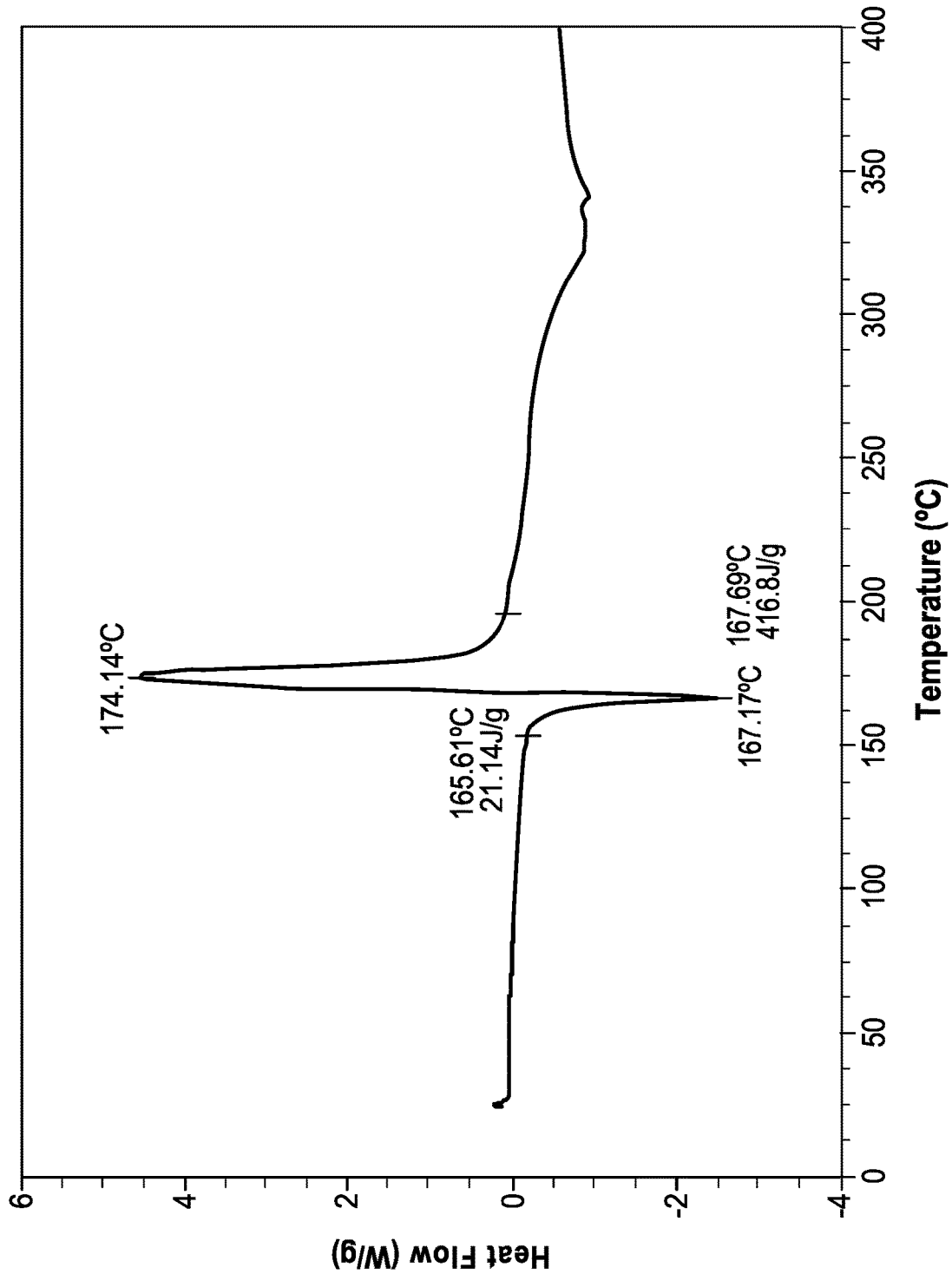
FIG. 7 depicts the characteristic DSC thermogram for the naphthalene sulfonic acid salt of compound F.
Figure 8:
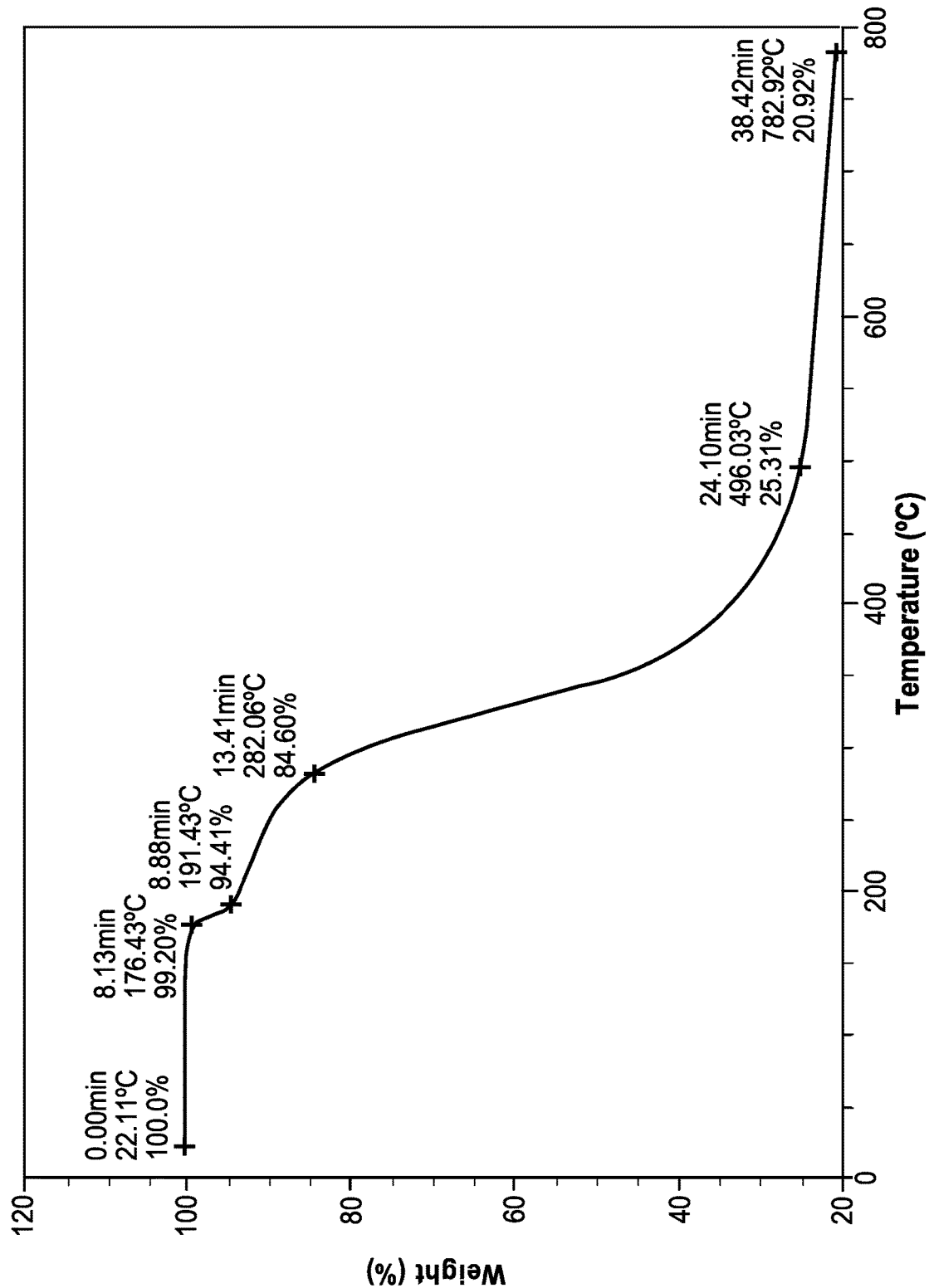
FIG. 8 depicts the characteristic thermogravimetric analysis ("TGA") data for the naphthalene sulfonic acid salt of compound F.
Figure 9:
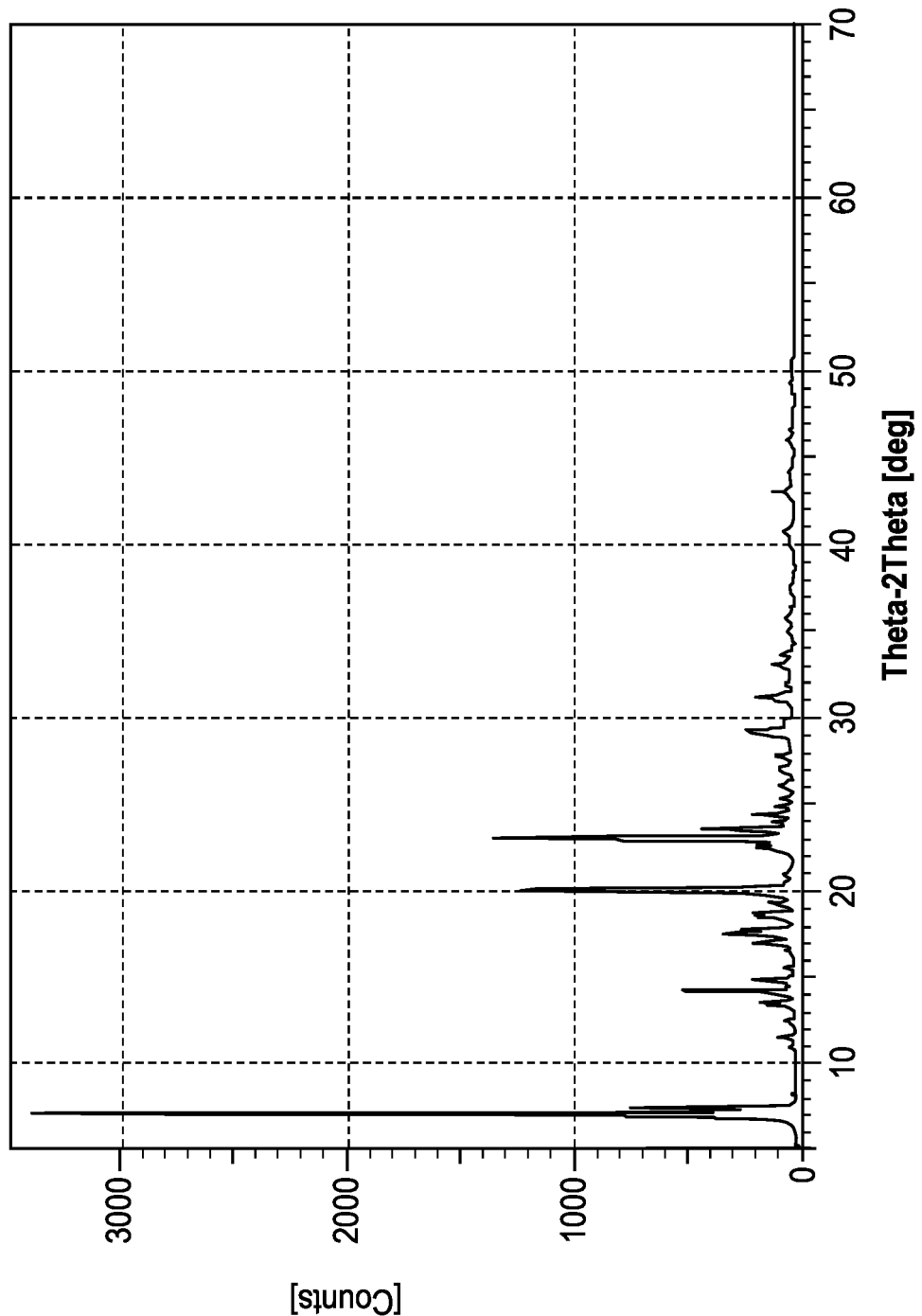
FIG. 9 depicts the characteristic XRPD pattern for the tosylate salt of compound F.

Compound F can be crystallized to form a polymorph, characterized by the differential scanning calorimetry ("DSC") thermogram, thermogravimetric analysis ("TGA") data, and X-ray power diffraction ("XRPD") pattern depicted in FIGS. 5, 6, 7, 8, and 9. Thus, another aspect of the present disclosure is a crystalline form of compound F, such as the tosylate salt of compound F, which is characterized by an XRPD pattern comprising peaks at 6.8, 7.1, 7.4, 14.2, 14.8, 17.0, 17.5, 17.8, 18.5, 18.7, 20.1, 20.3, 23.0, 23.6, 24.5, 29.3, and 31.2±0.2° 2θ using Cu Kα radiation, as shown in FIG. 9.

Figure 10:
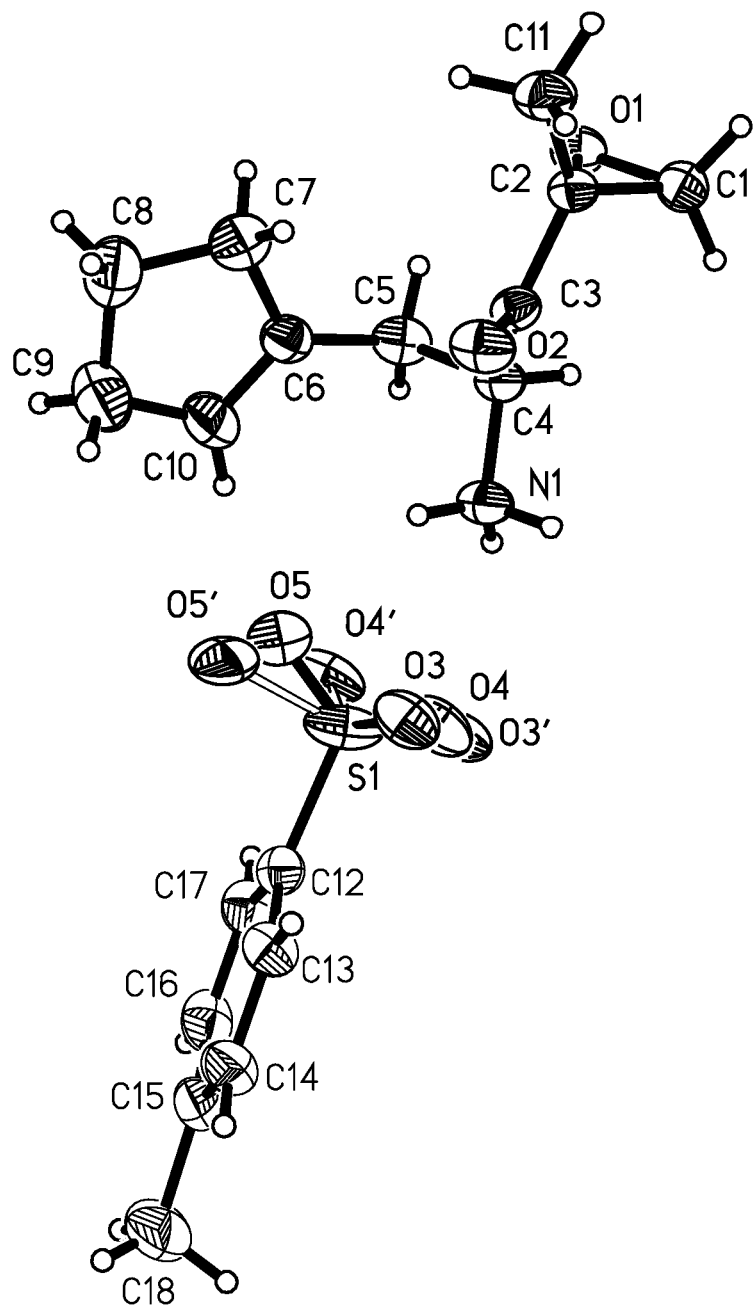
FIG. 10 depicts a single crystal X-ray diffraction ("XRD") of the tosylate salt of compound F.

The tosylate form of compound F also can be characterized by a single crystal X-ray diffraction ("XRD") structure, as described in the Examples section below. The crystal, as represented in FIG. 10, has a unit cell dimension of a=13.264(3) Å, a=90°, b=5.6920(11) Å, b=109.410(4)°, c=13.416(3) Å, g=90° and belongs to the space group P 21. The Flack parameter is 0.03 (0.08 su). Crystallizations that used other acids such as 2-napthalenesulfonic, methanesulfonic, benzenesulfonic, phosphoric, and sulfuric acid did not provide x-ray quality crystals in the following solvents: toluene, diethyl ether, MTBE, 1,4-dioxane, ethyl acetate, acetone, acetonitrile, butanol, isopropanol, and hexane/ethyl acetate (1:1 ratio).

For example, compound F can be prepared by (a) admixing together an aprotic solvent (e.g., DCM), TFA, and compound H at a molar ratio of 8:1 and a temperature of about 0° C., under a nitrogen atmosphere, for a time period of up to 2 hours, (b) concentrating the mixture at a temperature of about 15° C. to 25° C., and (c) admixing the concentrated mixture and an acid (e.g., p-toluenesulfonic acid) at temperature of about 0° C. for a time period of 10 to 12 hours. The resulting compound F can be filtered at about 0° C., washed with a polar, aprotic solvent (e.g., MBTE), and dried under vacuum.

Preparation of Compound D

In another aspect, provided herein is method for preparing compound D.

Compound D can be prepared in two steps-step (a) and step (b). In step (a), a mixture is prepared by admixing together a tertiary amine base and a suspension of compound B and compound C in an aprotic solvent: (i) (2S,3R)-1-(benzyloxy)-3-hydroxy-3-(4-methoxyphenyl)-1-oxopropan-2-aminium salt (compound "B"):

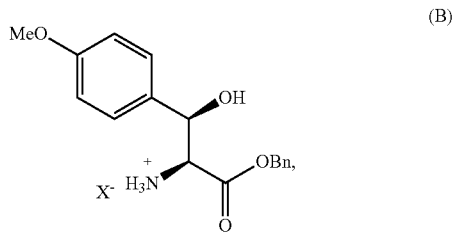

(B)

wherein X⁻ is a counterion, and (ii) (2-morpholinoacetyl)-L-alanine (compound "C"):

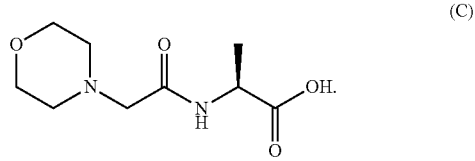

(C)

In step (b), the mixture from step (a) and a coupling agent are admixed together at a temperature in a range of about −5° C. to about 5° C. to form compound D.

The counterion (X⁻) can be any anion capable of forming an ionic bond with the ammonium group of compound B. In some embodiments, X⁻ is selected from the group consisting of tosylate, triflate, acetate, naphthalene sulfonate, 4-nitrobenzenesulfonate, sulfate, methylsulfate, nitrate, fluoride, chloride, bromide, and combinations thereof. In some cases, X⁻ can be tosylate, naphthalene sulfonate, or 4-nitrobenzenesulfonate. For example, X⁻ can be chloride.

The aprotic solvent can be any aprotic solvent (or mixture of solvents) in which the nucleophilic acyl substitution reaction between compounds B and C can proceed. Suitable aprotic solvents can include acetonitrile ("ACN"), dichloromethane ("DCM"), tetrahydrofuran ("THF"), dimethylacetamide ("DMAc"), ethyl acetate ("EtOAc"), isopropyl acetate ("iPrOAc"), dimethylformamide ("DMF"), and combinations thereof. For example, the aprotic solvent can include ACN.

Compound B and compound C can be present in a molar ratio of about 0.65:1 to 1.1:1. In some embodiments, compounds B and C are present in a ratio of about 0.75:1 to 1:1. For example, the molar ratio of compounds B and C can be about 0.8:1.

The tertiary amine base can be any tertiary amine base that can promote or catalyze the nucleophilic acyl substitution reaction between compounds B and C. Suitable tertiary amine bases can include, for example, N,N-diisopropylethylamine ("DIPEA"), triethylamine ("TEA"), N-methylmorpholine ("NMM"), 2,2,6,6-tetramethylpiperidine ("TMP"), 2,4,6-trimethylpyridine ("collidine"), or combinations thereof. For example, the tertiary amine base can include DIPEA. The tertiary amine base can be present in a molar ratio to compound B in a range of about 1:1 to about 3.5:1. For example, the molar ratio of tertiary amine base to compound B can be about 3.5:1.

The coupling agent can include, for example, a carbodiimide reagent, a phosphonium reagent, a uronium reagent, an immonium reagent, an imidazolium reagent, an organophosphorus reagent, an acid chloride reagent, a chloroformate reagent, a pyridinium reagent, or combinations thereof, as previously described above for the preparation of compound G. Examples of the carbodiimide reagent, phosphonium reagent, uronium reagent, immonium reagent, imidazolium reagent, organophosphorus reagent, acid chloride reagent, chloroformate reagent, and pyridinium reagent are described above for the preparation of compound G. In some embodiments, the uronium agent can include HATU, HBTU, and combinations thereof. For example, the uranium agent can be HATU. The coupling agent can be present in a molar ratio to compound B in a range of about 1:1 to about 1:3. In some embodiments, the coupling agent and compound B are present in a ratio of about 1:1 to 1:2. For example, the ratio of the coupling agent to compound B can be about 1:1.5.

The coupling reaction can be performed in the presence of a coupling additive.

Examples of coupling additives amounts thereof are described for the preparation of compound G.

The temperature of each admixing step is maintained in a range of about −5° C. to about 5° C. In some embodiments, the temperature of each admixing step is maintained at about 0° C. The temperature of each admixing step can be the same or different.

In step (b) of the preparation of compound D, the admixing can include mixing portions of the coupling agent with the mixture from step (a) over a time period of at least 1 minute up to about 30 minutes (e.g., up to about 5, 6, 7, 8, 9, 10, 11, 12, 13, 14, 15, 16, 16, 18, 19, 20, 21, 22, 23, 24, 25, 26, 27, 28, 29, or 30 minutes). In some embodiments, portions of the coupling agent can be added to the mixture from step (a) over a time period of at least about 1 minute (e.g., at least about 2, 3, 4, 5, 6, 7, 8, 9, 10, 11, 12, 13, 14, 15, 16, 17, 18, 19, 20, 21, 22, 23, 24, 25 minutes). For example, portions of the coupling agent can be added to the mixture from step (a) for a time period of about 1 minute to about 30 minutes or about 10 minutes to about 30 minutes, or about 20 minutes to about 30 minutes. The admixing of step (b) can also include stirring the mixture for up to about 3 hours (e.g., up to about 1, 1.5, 2, 2.5, or 3 hours). In some embodiments, the stirring can occur for up to about 2 hours. In some cases, the stirring can occur for at least about 30 minutes, or at least about 1 hour, or at least about 1.5 hours. For example, the stirring can occur for about 30 minutes to about 3 hours, or about 30 minutes to about 2.5 hours, or about 1 hour to about 2 hours.

After step (b), compound D can be quenched and/or washed with one or more solvents at a temperature in a range of about 15° C. to about 25° C. Suitable solvents for the quenching and/or washing include, for example, water, isopropyl acetate, potassium phosphate monobasic, sodium bicarbonate, sodium sulfate, THF, and combinations thereof.

For example, compound D can be prepared by (a) admixing together compound B and compound (C) (1:1 molar ratio) and a tertiary amine base (e.g., DIPEA) in ACN, and (b) admixing the mixture from step (a) and about 1 molar equivalent of HATU in portions over a time period of about 30 minutes, and then stirring the mixture for a time period of up to about 2 hours, wherein the temperature of each step is about 0° C. The resulting mixture from step (b) can be quenched with, for example, sodium bicarbonate to form a biphasic mixture. The organic phase can be separated and washed with sodium bicarbonate, potassium phosphate monobasic, and/or sodium sulfate.

Preparation of Compound B

Compound B can be prepared by admixing (i) an acid and (ii) benzyl (2S,3R)-2-((tert-butoxycarbonyl)amino)-3-hydroxy-3-(4-methoxyphenyl)propanoate (compound "A"):

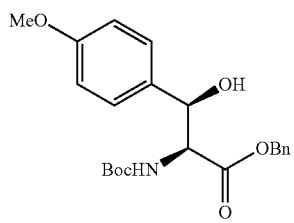

(A)

in an aprotic solvent.

The acid can be any suitable acid capable of deprotecting the amino group on compound A. Suitable acids include, for example, p-toluenesulfonic acid, trifluoromethanesulfonic acid, acetic acid, trifluoroacetic acid, naphthalene sulfonic acid, 4-nitrobenzenesulfonic acid, sulfonic acid, methylsulfonic acid, nitric acid, HF, HCl, HBr, and combinations thereof. In some embodiments, the acid includes trifluoroacetic acid or HCl.

The aprotic solvent can be any solvent in which the deprotection reaction can occur. Suitable solvents include ethyl acetate, N-methylpyrrolidone ("NMP"), tetrahydrofuran ("THF"), acetone, dimethylformamide ("DMF"), acetonitrile ("ACN"), dimethyl sulfoxide ("DMSO"), dicholormethane ("DCM"), and combinations thereof. For example, the solvent can include ethyl acetate, DCM, or a combination thereof.

In some embodiments, the temperature of the mixture during the admixing step is maintained in a range of about 15° C. to about 25° C., or at about 20° C.

In some embodiments, after completion of the admixing, compound B is filtered and dried under vacuum to form a crystalline polymorph, which is characterized by the DSC thermogram depicted in FIG. 1. Thus, another aspect of the present disclosure is a crystalline form of compound B, which is characterized by an XRPD pattern comprising peaks at 4.6, 9.2, 13.8, 18.5, and 32.9±0.2° 2θ using Cu Kα radiation.

For example, compound B can be prepared by admixing together an acid (e.g., HCl) and compound A at 20° C., filtering, and drying the resulting compound B.

Examples

The following examples are provided for illustration and are not intended to limit the scope of the invention.

General Synthetic Scheme

Compound G can be prepared according to Scheme 1, shown above.

Example 1: Large-Scale Preparation of the HCl salt of (2S,3R)-1-(benzyloxy)-3-hydroxy-3-(4-methoxyphenyl)-1-oxopropan-2-aminium salt (Compound "B")

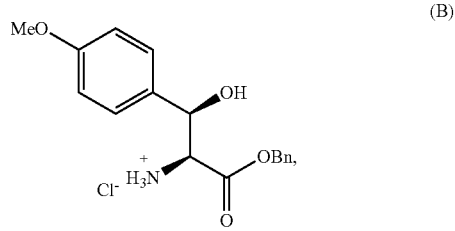

(B)

Ethyl acetate (58.5 kg) at 20° C. was charged with HCl gas (6.8 kg). To this solution was dissolved benzyl (2S,3R)-2-((tert-butoxycarbonyl)amino)-3-hydroxy-3-(4-methoxyphenyl)propanoate (compound "A"):

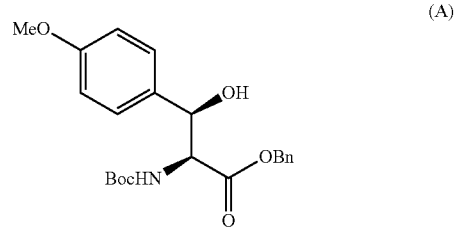 [SMILES: COc1ccc([C@@H](O)[C@H](NC(=O)OC(C)(C)C)C(=O)OCc2ccccc2)cc1]

(A)

(5 kg, 12.5 mol, pre-dissolved in 32.5 kg ethyl acetate). The suspension was stirred at 20° C. and upon completion, as determined by HPLC, was filtered and dried under vacuum at 45° C. to provide a crystalline polymorph of compound B (3.85 kg) as the HCl salt. LC/MS (LRMS (MH) m/z: 302). HPLC Purity 97.9%. The characteristic DSC curve is shown in FIG. 1.

Example 2: Small-Scale Synthesis of the TFA Salt of (2S,3R)-1-(benzyloxy)-3-hydroxy-3-(4-methoxyphenyl)-1-oxopropan-2-aminium salt (Compound "B")

Trifluoroacetic acid ("TFA") (20 mL) was added to a solution of compound A (7.0 g, 17.4 mmol) in dicholormethane ("DCM") (50 mL) at 0° C. The mixture was stirred for 30 min then diluted with DCM (100 mL). Saturated NaHCO$_3$ (aqueous, 100 mL) was added and the two layers were separated. The aqueous layer was extracted with DCM (2×100 mL) and the combined organic layers were dried over anhydrous sodium sulfate then concentrated to afford crude compound B (5.0 g, 84% yield) as the TFA salt. LC/MS (LRMS (MH) m/z: 302.

Example 3: Large-Scale Preparation of (2S,3R)-3-hydroxy-3-(4-methoxyphenyl)-2-((S)-2-(2-morpholinoacetamido)propanamido)propanoate (Compound "D")

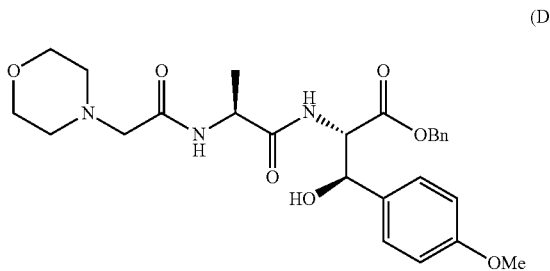

To compound B (3.8 kg) and (2-morpholinoacetyl)-L-alanine (compound "C"):

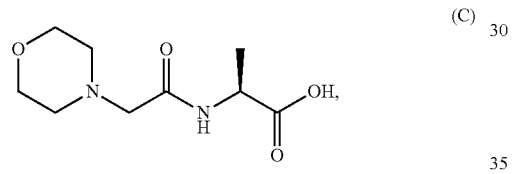

(2.5 kg) at 20° C. was added acetonitrile (30.4 kg). The temperature was adjusted to 0° C. and N,N-diisopropylethylamine ("DIPEA") (3.19 kg) was added, followed by 1-[Bis(dimethylamino)methylene]-1H-1,2,3-triazolo[4,5-b]pyridinium 3-oxid hexafluorophosphate ("HATU") (5.22 kg) portion-wise over 30 min. The reaction mixture was stirred for 2 h at 0° C. then quenched with 3.5% NaHCO$_3$ (aqueous, 46 kg) and stirred for 30 min. After standing for 1 h at 20° C., NaHCO$_3$ solid was added and the mixture was stirred for 30 min then allowed to stand again at 20° C. for 1 h. The aqueous layer was diluted with water (30.6 kg), extracted with isopropyl acetate ("iPrOAc") (23.4 kg), and the organic layers were combined. The organic layers were chased with iPrOAc (3×27 kg), washed with 3.5% NaHCO$_3$ (aqueous, 30 kg), KH$_2$PO$_4$ (aqueous, 3×65 kg), water (15 kg), 7% NaHCO$_3$ (aqueous, 2×61 kg), and 5% Na$_2$SO$_4$ (aqueous, 3×55 kg). The solution was concentrated to 18 L then chased with tetrahydrofuran ("THF") (4×22.8 L) to provide the product (5.04 kg, 90% yield, 97.9% purity by HPLC) as a solution in THF (34.5 wt %, 14.6 kg total).

Similar results were obtained using 1-ethyl-3-(3-dimethylaminopropyl)carbodiimide HCl ("EDC") (1.1 equiv.) in place of HATU as a coupling reagent.

Example 4: Small-Scale Synthesis of Compound D

The reagents HATU (6.79 g, 17.9 mmol) and DIPEA (9.63 mL, 59.2 mmol) were added to a solution of compound B (TFA salt, 5.0 g, 14.8 mmol) and compound C (3.36 g, 15.9 mmol) in dimethylformamide ("DMF") (100 mL) at 0° C. The reaction mixture was allowed to warm to room temperature and stirred for 1 h. The mixture was concentrated and the residue was purified by flash column chromatography on silica gel (petroleum ether/EtOAc=2:1 to 1:2) to afford compound D (5.8 g, 78% yield) as a colorless solid. LC/MS (LRMS (MH) m/z: 500.

Example 5: Large-Scale Preparation of (2S,3R)-3-hydroxy-3-(4-methoxyphenyl)-2-((S)-2-(2-morpholino-acetamido)propanamido)propanoic acid (compound "E")

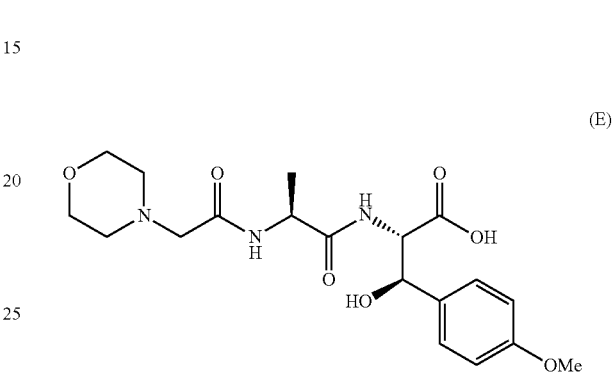

To a solution of benzyl (2S,3R)-3-hydroxy-3-(4-methoxyphenyl)-2-((S)-2-(2-morpholinoacetamido)propanamido)propanoate (compound "D") (5.04 kg as a 34.5% wt solution in THF) was added THF (3.25 kg) followed by methanol (7.0 kg). A N$_2$ atmosphere was established within the reaction vessel and Pd/C (10%, 473 g) was added under nitrogen protection. THF (500 g) and methanol (1 kg) were added to wash the reaction vessel and an H$_2$ atmosphere was established (15 psi). The reaction was stirred for 4 h at 17° C. then filtered across diatomite. The wet cake was washed with methanol (30 kg), concentrated to 3-4 volume, chased with THF (4×45 kg), and heated to 60-70° C. After 2 h the temperature was adjusted to 50-60° C. and THF (30 kg) was added. The mixture was again heated to 60-70° C. for 2 h. To this solution was added water (370 kg) at 60-70° C., then the mixture was cooled to 55-65° C. Seed crystal (18.0 g) was added and the mixture was stirred at 55-65° C. for 1 h. Twice the suspension was concentrated to 5-6 volumes and stirred for 2 h at 0° C. The mixture was filtered using THF (10 kg) to wash. The wet cake was dried to provide a crystalline polymorph of compound E (3.54 kg, 97.6% purity). Characteristic DSC, TGA, and XRPD data is shown in FIGS. 2-4.

Example 6: Small-Scale Synthesis of Compound E

To a solution of compound D (5.8 g, 11.6 mol) in THF (120 mL) was added Pd/C (1.5 g, 10%). The mixture was stirred under an H$_2$ atmosphere (1 atm) at ambient temperature overnight then filtered through a pad of celite. The filtrate was concentrated under reduced pressure and the residue was washed with EtOAc (20 mL) to afford Compound E (4.8 g, ~100% yield) as a colorless solid.

Example 7: Large-Scale Preparation of the Tosylate Salt of (S)-3-(cyclopent-1-en-1-yl)-1-((R)-2-methyloxiran-2-yl)-1-oxopropan-2-aminium salt (compound "F")

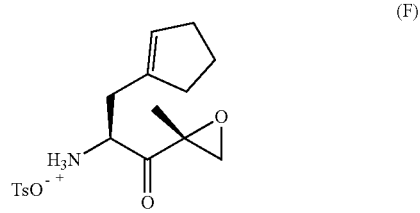

(F)

To a solution of tert-butyl ((S)-3-(cyclopent-1-en-1-yl)-1-((R)-2-methyloxiran-2-yl)-1-oxopropan-2-yl)carbamate (compound "H"):

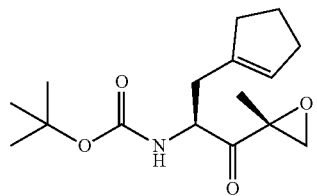

(H)

Figure 5:
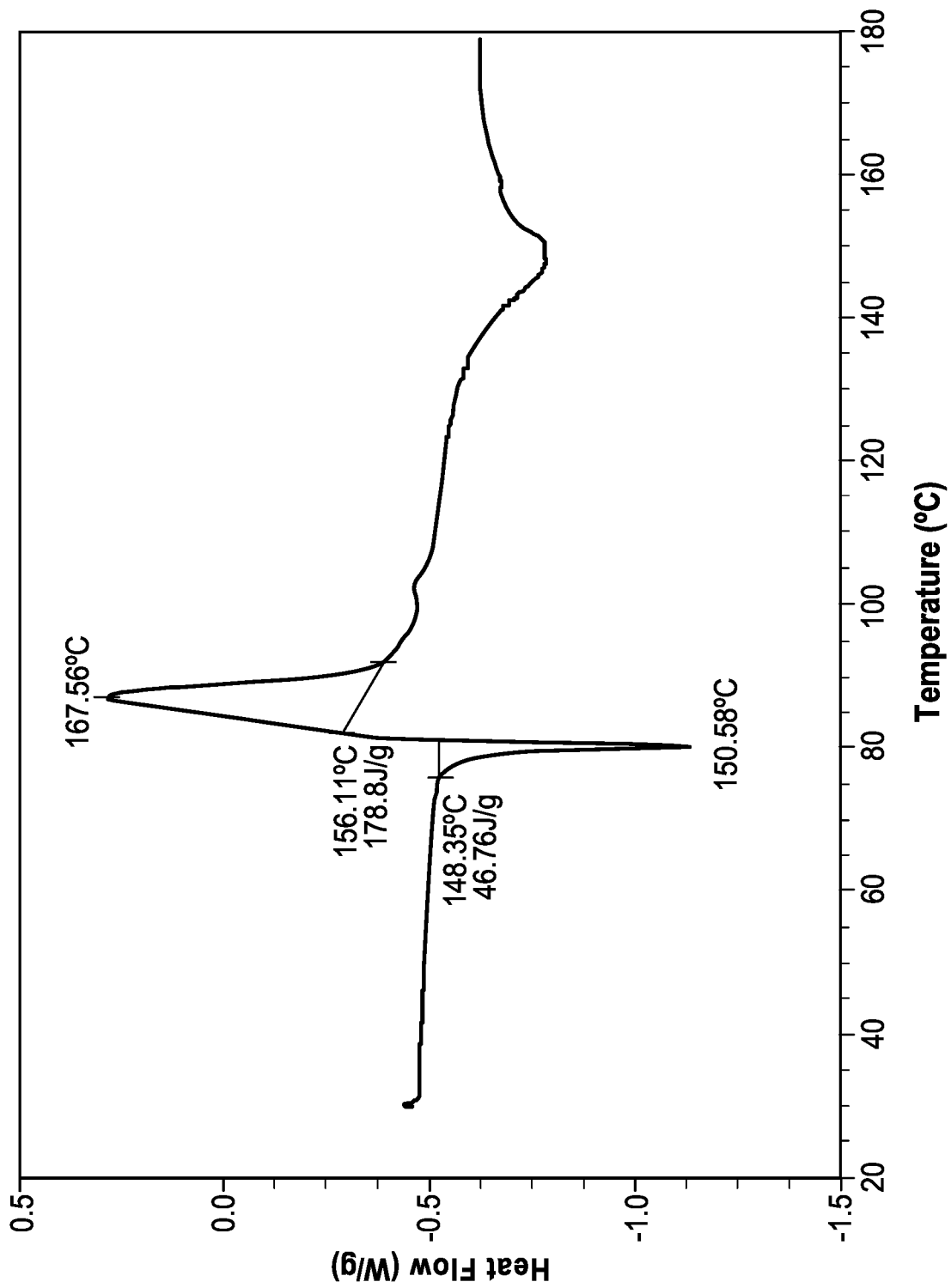
FIG. 5 depicts the characteristic DSC thermogram for the tosylate salt of (S)-3-(cyclopent-1-en-1-yl)-1-((R)-2-methyloxiran-2-yl)-1-oxopropan-2-aminium salt (compound "F").
Figure 6:
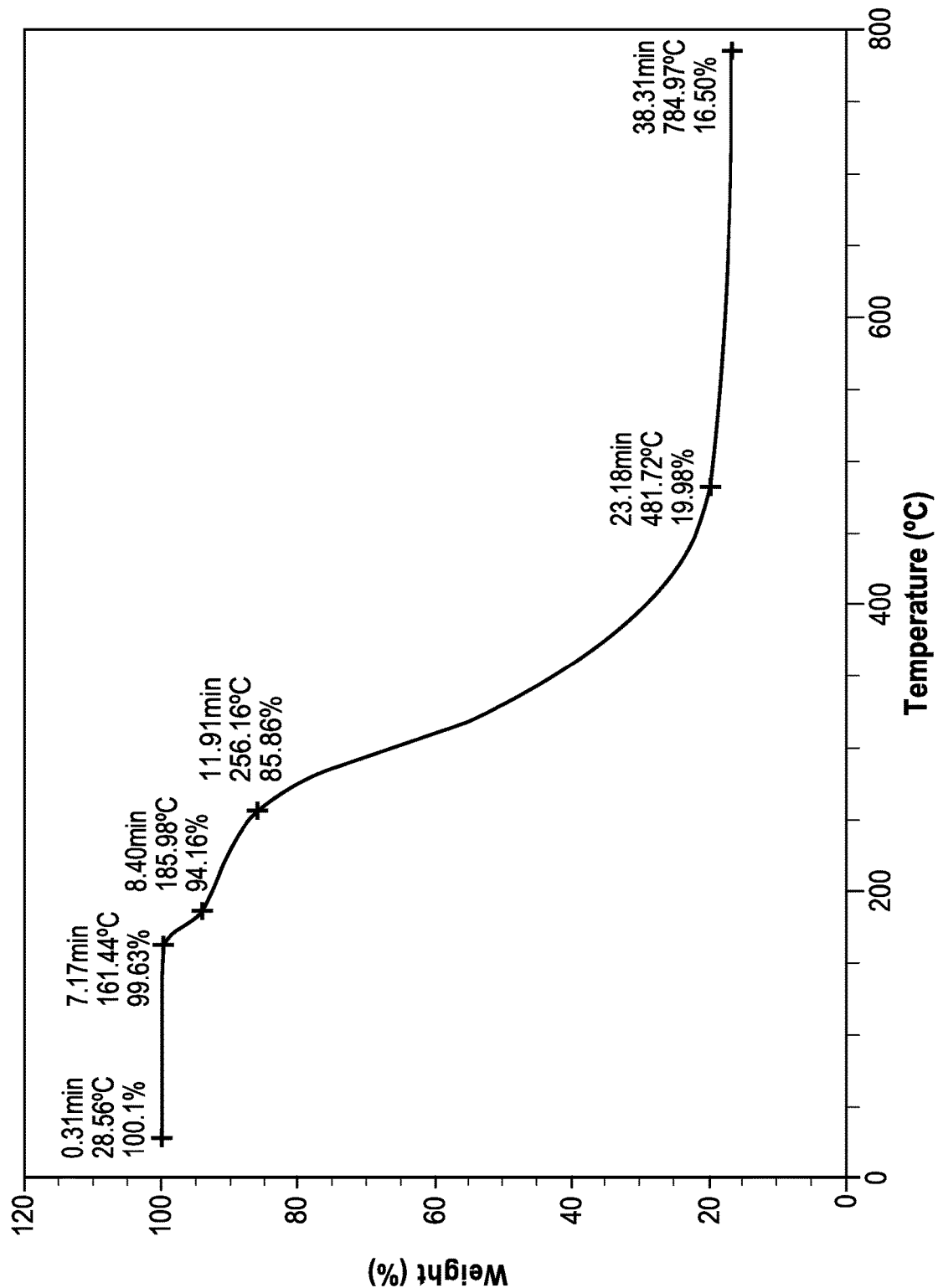
FIG. 6 depicts the characteristic thermogravimetric analysis ("TGA") data for the tosylate salt of compound F.

(134 g) in DCM (402 mL) at 0° C. was added TFA (414.3 g, 8 eq) at a rate to maintain the internal temperature at −5-5° C. The reaction mixture was stirred for 2 h at this temperature under $N_2$. The dark mixture was then concentrated to remove DCM and TFA at 15-25° C. The solution was chased with methyl tert-butyl ether ("MBTE") (5×2 L). HPLC analysis indicated 2.72 eq TFA remained in the solution and MTBE (804 mL) was added at 15-25° C. To this solution at 0° C. was added p-toluenesulfonic acid ("PTSA") (83.6 g) and the mixture was stirred at this temperature for 10-12 h. The mixture was then filtered at 0° C., washed with MTBE (3×268 mL then 1×168 mL), and the filter cake was dried under vacuum at 15-25° C. for 16-18 h to provide compound F (126 g, 99.4% purity) as the tosylate salt. Characteristic DSC and TGA curves are shown in FIGS. 5 and 6, and a characteristic XRPD pattern can be found in FIG. 9.

Example 8: Small-Scale Synthesis of the Naphthalene Sulfonate Salt of Compound F To compound H (2 g) was added DCM (8 mL) and the mixture was cooled to 5° C. TFA (8 mL) was added at a rate to maintain the internal temperature below 10° C. The mixture was then stirred at ambient temperature for 30 min then concentrated under vacuum. Toluene (3×5 mL) was added to remove excess TFA. To the TFA salt was added EtOAc (4 mL) followed 2-napthalenesulfonic acid (6.78 mmol, 1.41 g, dissolved in 10 mL EtOAc). The mixture was stirred at ambient temperature and a colorless solid precipitated within 5 min. The mixture was stirred an additional 15 min then filtered using EtOAc (10 mL) to rinse. The solid was placed under vacuum for 16 h to provide the naphthalene sulfonate salt as a colorless solid (1.62 g, 72% yield). Characteristic DSC and TGA data are shown in FIGS. 7 and 8.

A similar procedure was used to generate the 4-nitrobenzenesulfonic acid of Compound F.

Example 9: Large-Scale Preparation of (2S,3R)—N-[(2S)-3-(cyclopent-1-en-1-yl)-1-[(2R)-2-methyloxiran-2-yl]-1-oxopropan-2-yl]-3-hydroxy-3-(4-methoxyphenyl)-2-[(2S)-2-[2-(morpholin-4-yl)acetamido]propanamido]propanamide (Compound "G")

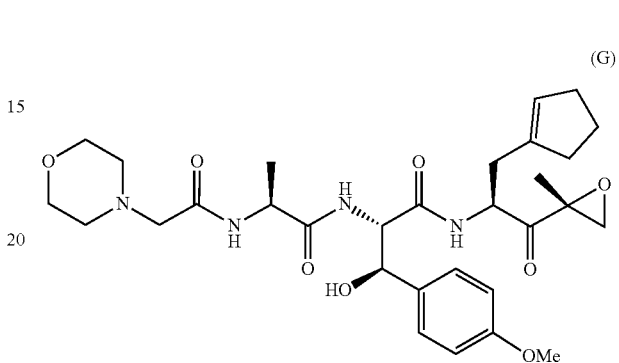

(G)

To Compound E (110.0 g) and Compound F (tosylate salt, 110.0 g) was added DCM (1.46 kg) and the suspension was cooled to −15 to −5° C. DIPEA (122.1 g) was added at a rate to maintain an internal temperature of −15 to −5° C. The mixture was then stirred for 10 min and to this solution was added HATU (114.4 g) at −15 to −5° C. under nitrogen. The mixture was stirred for 2 h at −15 to −5° C. and compound F (3.91 g) was added. After 10 min, the internal temperature was adjusted to 5 to 15° C. then water (1100 g) was added. The solution was stirred for 30-60 min and allowed to stand for 30-60 min. The organic layer was separated and washed with water (1100 g) for 30-60 min and the mixture was allowed to stand for 30-60 min. The organic phases were combined and the temperature was raised to 15 to 25° C. The solution was concentrated to 2-4 volumes under vacuum (<45° C.). iPrOAc (957 g) was added and the solution was concentrated to 2-4 volumes under vacuum (<45° C.). The solution was washed with 5% $KH_2PO_4$ (aqueous, 1100 g), 1% $KH_2PO_4$ (aqueous, 2×1100 g), 7% $NaHCO_3$ (aqueous, 1100 g), and 5% $Na_2SO_4$ (aqueous, 1100 g). The product was provided as a 10.53 wt % solution in iPrOAc (89.8%).

Example 10: Small-Scale Preparation of Compound G

HATU (5.35 g, 14.1 mmol) and DIPEA (9.55 mL, 58.7 mmol) were added to a solution of compound E (4.8 g, 11.7 mmol) and compound F (TFA salt, 3.46 g, 11.7 mmol) in DMF (90 mL) at 0° C. The reaction mixture was allowed to warm to room temperature and stirred for 30 min. The mixture was concentrated and the residue was purified by flash column chromatography on silica gel (petroleum ether/EtOAc=2:1 to EtOAc) to afford Compound G (4.8 g, 70% yield, 95.2% purity by HPLC) as a colorless solid. LC/MS (LRMS (MH) m/z: 587).

Example 11: Preparation of a Single Crystal of the Tosylate Salt of Compound F The TFA salt of compound F (0.70 g, 2.39 mmol) was dissolved in MTBE (3.5 mL) and p-toluenesulfonic acid (0.45 g, 2.39 mmol) was added. The solution was sealed in a vial and allowed to stand at ambient temperature. After 9 months, the solvent was removed from the precipitated crystals and the solid was allowed to dry at ambient temperature over 2 days. See Flack, H. D.; Bernardinelli, G. The Use of X-Ray Crystallography to Determine Absolute Configuration. *Chirality,* 2008, 20, 681-690.

Example 12: Comparison of Stability of Trifluoroacetic Acid and Tosylate Salts of Compound F The stability of the trifluoroacetic and tosylate salts of compound F were determined by exposing multiple lots of each salt to a temperature of 25° C. at a relative humidity of 40% for one or ninety days, and determining the percentage that each sample had decomposed. As shown in the table below, the tosylate salt of compound F is significantly more stable than its trifluoroacetic acid counterpart.

| Form | Lot # | % Purity at t = 0 | % Purity at Indicated Time (days) | % Decomposition |
|---|---|---|---|---|
| Tosylate | 1 | 97.2 | 96.0 (90) | 1.2 |
|  | 2 | 88.6 | 85.0 (90) | 3.6 |
| Trifluoroacetate | 3 | 85.3 | 79.6 (1) | 5.7 |
|  | 4 | 94.8 | 86.0 (1) | 8.8 |

The foregoing description is given for clearness of understanding only, and no unnecessary limitations should be understood therefrom, as modifications within the scope of the invention may be apparent to those having ordinary skill in the art.

Throughout this specification and the claims which follow, unless the context requires otherwise, the word "comprise" and variations such as "comprises" and "comprising" will be understood to imply the inclusion of a stated integer or step or group of integers or steps but not the exclusion of any other integer or step or group of integers or steps.

Throughout the specification, where compositions are described as including components or materials, it is contemplated that the compositions can also consist essentially of, or consist of, any combination of the recited components or materials, unless described otherwise. Likewise, where methods are described as including particular steps, it is contemplated that the methods can also consist essentially of, or consist of, any combination of the recited steps, unless described otherwise. The invention illustratively disclosed herein suitably may be practiced in the absence of any element or step which is not specifically disclosed herein.

The practice of a method disclosed herein, and individual steps thereof, can be performed manually and/or with the aid of or automation provided by electronic equipment. Although processes have been described with reference to particular embodiments, a person of ordinary skill in the art will readily appreciate that other ways of performing the acts associated with the methods may be used. For example, the order of various of the steps may be changed without departing from the scope or spirit of the method, unless described otherwise. In addition, some of the individual steps can be combined, omitted, or further subdivided into additional steps.

All patents, publications and references cited herein are hereby fully incorporated by reference. In case of conflict between the present disclosure and incorporated patents, publications and references, the present disclosure should control.

We claim:

1. A method of preparing benzyl (2S,3R)-3-hydroxy-3-(4-methoxyphenyl)-2-((S)-2-(2-morpholinoacetamido)propanamido)propanoate (compound "D")

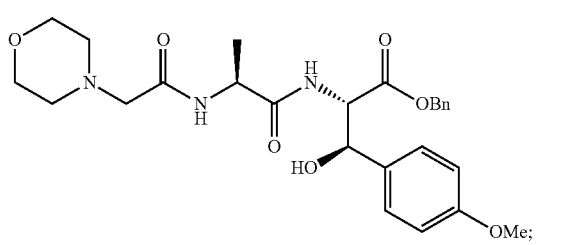

comprising:
(a) admixing a tertiary amine base and a suspension of:
(i) (2S,3R)-1-(benzyloxy)-3-hydroxy-3-(4-methoxyphenyl)-1-oxopropan-2-aminium salt (compound "B"):

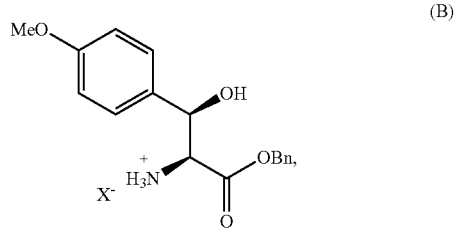

wherein X⁻ is a counterion; and
(ii) (2-morpholinoacetyl)-L-alanine (compound "C"):

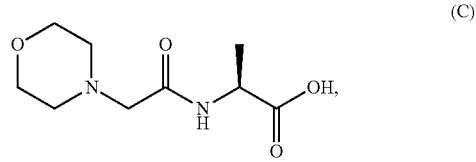

in an aprotic solvent to form a mixture; and
(b) admixing a coupling agent and the mixture of step (a) to form compound D;
wherein the temperature of each admixing step is maintained at −5° C. to 5° C.

2. The method of claim 1, wherein X⁻ is selected from the group consisting of tosylate, triflate, acetate, naphthalene sulfonate, 4-nitrobenzenesulfonate, sulfate, methylsulfate, nitrate, fluoride, chloride, bromide, and combinations thereof.

3. The method of claim 1, wherein the aprotic solvent is selected from the group consisting of acetonitrile ("ACN"), dichloromethane ("DCM"), tetrahydrofuran ("THF"), dimethylacetamide ("DMAc"), and combinations thereof.

4. The method of claim 1, wherein the tertiary amine base is selected from the group consisting of N,N-diisopropylethylamine ("DIPEA"), triethylamine ("TEA"), N-methylmorpholine ("NMM"), 2,2,6,6-tetramethylpiperidine ("TMP"), 2,4,6-trimethylpyridine ("collidine"), and combinations thereof.

5. The method of claim 1, wherein the coupling agent comprises a carbodiimide reagent, a phosphonium reagent, a uronium reagent, an immonium reagent, an imidazolium reagent, an organophosphorus reagent, an acid chloride reagent, a chloroformate reagent, or a pyridinium reagent.

6. The method of claim 5, wherein the uronium reagent is selected from the group 1-[Bis(dimethylamino)methylene]-1H-1,2,3-triazolo[4,5-b]pyridinium 3-oxid hexafluorophosphate ("HATU"), O-(Benzotriazol-1-yl)-N,N,N',N'-tetramethyluronium hexafluorophosphate ("HBTU"), and combinations thereof.

7. The method of claim 1, wherein the molar ratio of coupling agent to compound B is 1 to 1.

8. The method of claim 1, wherein the coupling reagent further comprises a coupling additive.

9. The method of claim 8, wherein the coupling additive is selected from the group consisting of a benzotriazole, a dicarboximide, a succinimide, and combinations thereof.

10. The method of claim 9, wherein the coupling additive is selected from the group consisting of N-hydroxysuccinimide ("HOSu"), N-hydroxy-5-norbornene-2,3-dicarboximide ("HONB"), 1-hydroxybenzotriazole ("HOBt"), 6-chloro-1-hydroxybenzotriazole ("Cl-HOBt"), 1-hydroxy-7-azabenzotriazole ("HOAt"), and combinations thereof.

11. The method of claim 1, wherein the temperature of each admixing step is maintained at −5° C. to 5° C.

12. The method of claim 1, wherein the admixing of step (b) comprises mixing portions of the coupling agent with the mixture from step (a) over 30 minutes.

13. The method of claim 1, wherein compound B is prepared by admixing (i) an acid and (ii) benzyl (2S,3R)-2-((tert-butoxycarbonyl)amino)-3-hydroxy-3-(4-methoxyphenyl)propanoate (compound "A"):

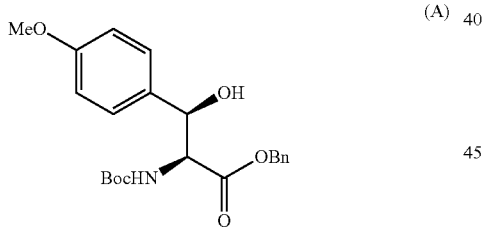

in a polar, aprotic solvent, to form compound B.

14. The method of claim 13, wherein the acid is selected from the group consisting of p-toluenesulfonic acid, trifluoromethanesulfonic acid, acetic acid, trifluoroacetic acid, naphthalene sulfonic acid, 4-nitrobenzenesulfonic acid, sulfonic acid, methylsulfonic acid, nitric acid, HF, HCl, HBr, and combinations thereof.

15. The method of claim 13, wherein the polar, aprotic solvent is selected from the group consisting of ethyl acetate, N-methyl pyrrolidone ("NMP"), tetrahydrofuran ("THF"), acetone, dimethylformamide ("DMF"), acetonitrile ("ACN"), dimethyl sulfoxide ("DMSO"), dicholormethane ("DCM"), and combinations thereof.

16. The method of claim 13, wherein the admixing step comprises stirring at a temperature in a range of 15° C. to 25° C.

17. A crystalline compound selected from:
(a) a crystalline form of (2S,3R)-1-(benzyloxy)-3-hydroxy-3-(4-methoxyphenyl)-1-oxopropan-2-aminium chloride salt (compound "B-Cl")

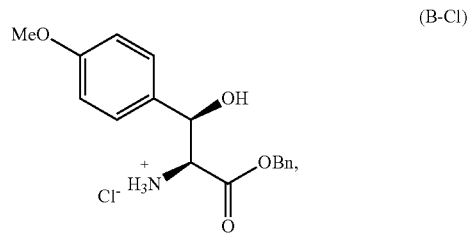 [SMILES: COc1ccc([C@@H](O)[C@H](N)C(=O)OCc2ccccc2)cc1 ; [Cl-]]

characterized by an X-ray powder diffraction pattern comprising peaks at 4.6, 9.2, 13.8, 18.5, and 32.9±0.2° 2θ using Cu Kα radiation, (b) a crystalline form of (2S,3R)-3-hydroxy-3-(4-methoxyphenyl)-2-((S)-2-(2-morpholinoacetamido)propanamido)propanoic acid (compound "E"):

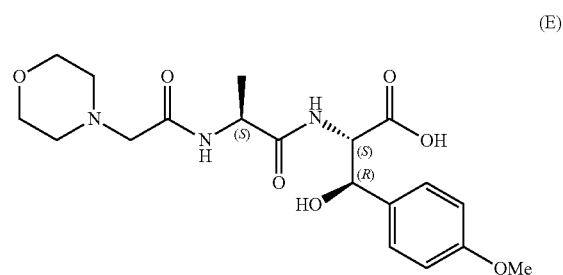

characterized by an X-ray powder diffraction pattern comprising peaks at 6.2, 8.5, 9.7, 12.7, 13.7, 16.0, 16.9, 17.2, 18.4, 18.9, 19.2, 19.7, 22.5, 24.7, 25.4, 28.7, and 29.7±0.2° 2θ using Cu Kα radiation; and (c) a crystalline form of (S)-3-(cyclopent-1-en-1-yl)-1-((R)-2-methyloxiran-2-yl)-1-oxopropan-2-aminium salt (compound "F"):

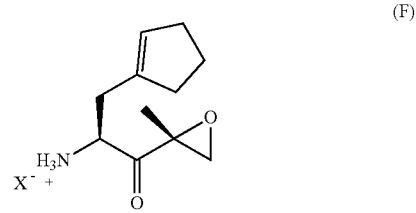

wherein X is tosylate,
characterized by an X-ray powder diffraction pattern comprising peaks at 6.8, 7.1, 7.4, 20.3, 23.0, 23.6, 24.5, 29.3, and 31.2±0.2° 2θ using Cu Kα radiation.

18. The crystalline compound of claim 17, wherein the crystalline compound is compound B-Cl.

19. The crystalline compound of claim 17, wherein the crystalline compound is compound E.

20. The crystalline compound of claim 17, wherein the crystalline compound is compound F tosylate.

* * * * *